United States Patent
Misztal et al.

(10) Patent No.: US 12,202,783 B2
(45) Date of Patent: Jan. 21, 2025

(54) METHOD FOR SYNTHESIS OF ORGANIC IODIDES, A PEROVSKITE-FORMING COMPOSITION COMPRISING AN ORGANIC IODIDE AND A PHOTOVOLTAIC CELL WITH A PEROVSKITE LAYER OBTAINED THEREFROM

(71) Applicant: SAULE S.A., Wroclaw (PL)

(72) Inventors: Kasjan Misztal, Wroclaw (PL); Konrad Wojciechowski, Wroclaw (PL); Olga Malinkiewicz, Wroclaw (PL); Zbigniew Miara, Dankowice (PL)

(73) Assignee: SAULE S.A., Wroclaw (PL)

( * ) Notice: Subject to any disclaimer, the term of this patent is extended or adjusted under 35 U.S.C. 154(b) by 582 days.

(21) Appl. No.: 17/601,065

(22) PCT Filed: Jun. 1, 2020

(86) PCT No.: PCT/IB2020/055167
§ 371 (c)(1),
(2) Date: Oct. 3, 2021

(87) PCT Pub. No.: WO2020/202131
PCT Pub. Date: Oct. 8, 2020

(65) Prior Publication Data
US 2022/0185765 A1  Jun. 16, 2022

(30) Foreign Application Priority Data
Apr. 2, 2019  (PL) .......................................... 429454

(51) Int. Cl.
| | | |
|---|---|---|
| C07C 209/00 | (2006.01) | |
| B01J 31/02 | (2006.01) | |
| C07C 257/12 | (2006.01) | |
| C07F 7/24 | (2006.01) | |
| C09D 11/52 | (2014.01) | |
| H10K 85/30 | (2023.01) | |
| H01G 9/20 | (2006.01) | |
| H10K 30/00 | (2023.01) | |

(52) U.S. Cl.
CPC ......... *C07C 209/00* (2013.01); *B01J 31/0235* (2013.01); *C07C 257/12* (2013.01); *C07F 7/24* (2013.01); *C09D 11/52* (2013.01); *H10K 85/30* (2023.02); *C01P 2002/34* (2013.01); *C01P 2002/72* (2013.01); *C01P 2004/03* (2013.01); *H01G 9/2059* (2013.01); *H10K 30/00* (2023.02)

(58) Field of Classification Search
CPC ............... B01J 31/0235; C01P 2002/34; C01P 2002/72; C01P 2004/03; C07C 209/00; C07C 211/03; C07C 211/04; C07C 211/06; C07C 211/07; C07C 257/12; C07F 7/24; C09D 11/52; H01G 9/2059; H10K 30/00; H10K 30/50; H10K 71/12; H10K 85/30; H10K 85/50
See application file for complete search history.

(56) References Cited

FOREIGN PATENT DOCUMENTS

| | | | |
|---|---|---|---|
| JP | 2018111618 | * | 7/2018 |
| JP | 2018111618 A | | 7/2018 |
| WO | 2014045021 A1 | | 3/2014 |
| WO | 2016088019 A1 | | 6/2016 |
| WO | WO2016/088019 | * | 6/2016 |

OTHER PUBLICATIONS

Zhang et al. (Ultrasmooth organic-inorganic perovskite thin-film formation and crystallization for efficient planar heterojunction solar cells, Nature Communications, pp. 1-10, Published 2015) (Year: 2015).*
JP2018111618 translation (Year: 2018).*
Wei Zhang et al: "Ultrasmooth organic-inorganic perovskite thin-film formation and crystallization for efficient planar heterojunction solar cells" Nature Communications, vol. 6, Jan. 30, 2015, DOI: 10.1038/ncomms7142 p. 8 Methods; table 1.
Joong-Gon Kim et al: "Facile and Highly Efficient N-Fomylation of Amines Using a Catalyic Amount of Iodine under Solvent-Free Conditions", Synlett, vol. 2010, No. 14. Jul. 22, 2010, pp. 2093-2096, XP055727498, DE ISSN:0936-5214, DOIE: 1001055/s-0030-1258518 table 1.
Bart Roose et al: "Spontaneous crystal coalescence enables highly efficient perovskite solar cells", Nano Energy, vol. 39, Sep. 1, 2017, pp. 24-29, XP055728657, ISSN: 2211-2855, DOI: 10.14016/j.nanoen.2017.06.037 p. 25, paragraph 2.4.

* cited by examiner

*Primary Examiner* — Yevgeny Valenrod
*Assistant Examiner* — Blaine G Doletski
(74) *Attorney, Agent, or Firm* — Rivka Friedman

(57) ABSTRACT

A method for obtaining a salt with a general formula: $R_xNI$, wherein: $R_xN$ is an organic cation ($R_xN^+$), R represents substituents (R—) independently selected from a group consisting of organic substituents: $R^1$—, $R^2$—, $R^3$— and hydrogen (H—), x is a number of the substituents R— directly linked with the nitrogen (N) atom in the organic cation $R_xN^+$, wherein x is 3 or 4, I is an iodide anion ($I^-$). The method comprises: preparing a reaction mixture comprising the steps of: synthesizing hydrogen iodide (HI) in situ by mixing molecular iodine ($I_2$) with formic acid (COOH) in a molar ratio of molecular iodine ($I_2$): formic acid (COOH) of no less than 1.01:1, in a solvent medium, introducing into the solvent medium a compound being a donor of organic cation $R_xN^+$ in an amount providing the molar ratio of the donor of organic cation $R_xN^+$: molecular iodine ($I_2$) of no less than 1.01:1, and maintaining the reaction mixture at a temperature of not less than 20° C. for the time necessary to obtain the reaction product being the salt with the general formula $R_xNI$. The obtained product is a substrate for synthesis of perovskites.

17 Claims, 14 Drawing Sheets

1. $I_2 + HCOOH \rightarrow 2 \, H^{+} I^{-} \, (\text{in situ}) + CO_2$

2. $H^{+} I^{-} +$ the donor of organic cation $R_xN \rightarrow R_xN^{+} I^{-}$ Summary:

3. $I_2 + HCOOH + 2$ the donor of organic cation $R_xN \rightarrow 2 R_xN^{+} I^{-} + CO_2$

Fig. 1A

1. $R_xN^{+} I^{-} + I_2 \rightarrow R_xN^{+} I_3^{-}$

2. $R_xN^{+} I_3^{-} + HCOOH \rightarrow R_xN^{+} I^{-} + 2 \, H^{+} I^{-} \, (\text{in situ}) + CO_2$ 3. $H^{+} I^{-} +$ the donor of organic cation $R_xN \rightarrow R_xN^{+} I^{-}$ Summary:

4. $I_2 + HCOOH + 2$ the donor of organic cation $R_xN \xrightarrow{R_xN^{+} I^{-}} 2 R_xN^{+} I^{-} + CO_2$

Fig. 1B

1. 
2. 
Summary:
3. 
Fig. 2A
1. 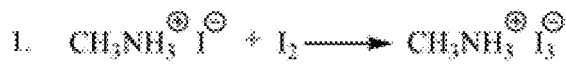
2. 
3. 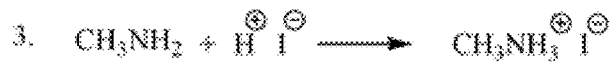
Summary:
4. 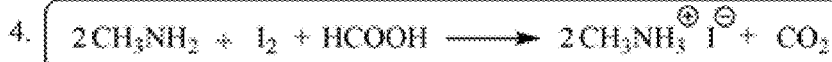
Fig. 2B

1. $I_2 + HCOOH \longrightarrow 2 H^\oplus I^\ominus + CO_2$

2. $CH_3(CH_2)_6CH_2NH_2 + H^\oplus I^\ominus \longrightarrow CH_3(CH_2)_6CH_2NH_3^\oplus I^\ominus$ Summary:

3. $2\ CH_3(CH_2)_6CH_2NH_2 + I_2 + HCOOH \longrightarrow 2\ CH_3(CH_2)_6CH_2NH_3^\oplus I^\ominus + CO_2$

Fig. 3A

1. $CH_3(CH_2)_6CH_2NH_3^\oplus I^\ominus + I_2 \longrightarrow CH_3(CH_2)_6CH_2NH_3^\oplus I_3^\ominus$ 2. $CH_3(CH_2)_6CH_2NH_3^\oplus I_3^\ominus + HCOOH \longrightarrow CH_3(CH_2)_6CH_2NH_3^\oplus I^\ominus + 2 H^\oplus I^\ominus + CO_2$ 3. $CH_3(CH_2)_6CH_2NH_2 + H^\oplus I^\ominus \longrightarrow CH_3(CH_2)_6CH_2NH_3^\oplus I^\ominus$ Summary:

4. $2\ CH_3(CH_2)_6CH_2NH_2 + I_2 + HCOOH \longrightarrow 2\ CH_3(CH_2)_6CH_2NH_3^\oplus I^\ominus + CO_2$

Fig. 3B

1. $I_2 + HCOOH \longrightarrow 2\,H^{\oplus}I^{\ominus} + CO_2$

2. $HC(NH_2)_2^{\oplus}\,CH_3COO^{\ominus} + H^{\oplus}I^{\ominus} \longrightarrow HC(NH_2)_2^{\oplus}\,I^{\ominus} + CH_3CHOOH$ Summary:

3. $\boxed{2\,HC(NH_2)_2^{\oplus}\,CH_3COO^{\ominus} + I_2 + HCOOH \longrightarrow 2\,HC(NH_2)_2^{\oplus}\,I^{\ominus} + CO_2 + CH_3COOH}$

Fig. 4A

1. $HC(NH_2)_2^{\oplus}\,I^{\ominus} + I_2 \longrightarrow HC(NH_2)_2^{\oplus}\,I_3^{\ominus}$ 2. $HC(NH_2)_2^{\oplus}\,I_3^{\ominus} + HCOOH \longrightarrow HC(NH_2)_2^{\oplus}\,I^{\ominus} + 2\,H^{\oplus}I^{\ominus} + CO_2$ 3. $HC(NH_2)_2^{\oplus}\,CH_3COO^{\ominus} + H^{\oplus}I^{\ominus} \longrightarrow HC(NH_2)_2^{\oplus}\,I^{\ominus} + CH_3COOH$ Summary:

4. $\boxed{2\,HC(NH_2)_2^{\oplus}\,CH_3COO^{\ominus} + I_2 + HCOOH \longrightarrow 2\,HC(NH_2)_2^{\oplus}\,I^{\ominus} + CO_2 + CH_3COOH}$

Fig. 4B

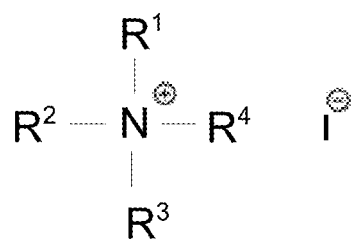
formula I
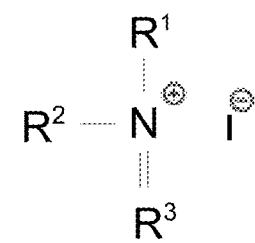
formula II
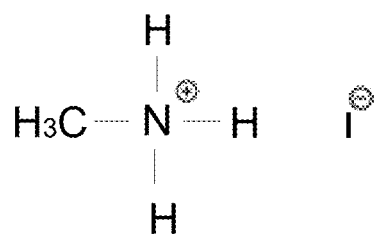
formula III (MAI)
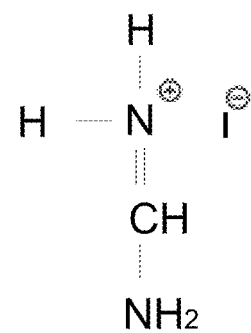
formula V (FAI)
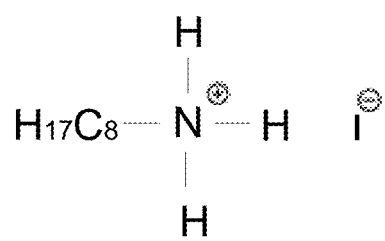
formula IV (OAI)
Fig. 5

1. $CH_3NH_3I + PbI_2 \rightarrow CH_3NH_3PbI_3$

2. $CH_3NH_3I + PbBr_2 \rightarrow CH_3NH_3Pb(Br_xI_{x-1})_3$

3. $CH_3NH_3I + PbCl_2 \rightarrow CH_3NH_3PbI_2Cl$

4. $NH_2CH=NH_2I + PbI_2 \rightarrow NH_2CH=NH_2PbI_3$

5. $CH_3NH_3I + SnI_2 \rightarrow CH_3NH_3SnI_3$

6. $CH_3NH_3I + SnBr_2 \rightarrow CH_3NH_3SnI_{3-x}Br_x$

Fig. 6

METHOD FOR SYNTHESIS OF ORGANIC IODIDES, A PEROVSKITE-FORMING COMPOSITION COMPRISING AN ORGANIC IODIDE AND A PHOTOVOLTAIC CELL WITH A PEROVSKITE LAYER OBTAINED THEREFROM

The invention relates to a method for obtaining salts, organic iodides, with a general formula $(R_xNI)$ featuring high purity of the obtained products, a perovskite-forming composition, suitable to be used in obtaining a perovskite photoactive coating, containing at least one iodide obtained using this method, and a photovoltaic cell with a perovskite photoactive layer formed using this composition.

Photoactive coatings are used to produce photovoltaic cells, i.e. semiconductor elements used to convert solar radiation into electricity. In photovoltaic cells, the photoactive layer acts as a sunlight (photon) absorber, so it is usually applied as a visible surface of the cell, coated with a suitable sunlight permeable (translucent/transparent) electrode material.

One of the known types of photoactive coatings are photoactive inks. One of the advantages of a photoactive ink is easy and inexpensive method of application of the ink onto the substrate: the ink is printed, wherein the choice of the printing technique depends on the production scale, the type of substrate and the physical properties of the ink, such as its viscosity and adhesive properties.

There are known organic photoactive inks containing organic film-forming substance in a form of doped polymers or monomers capable of polymerisation after its application onto the target substrate.

For example, a US patent application US20130087744 describes a composition of a photovoltaic ink consisting of polymeric precursors with a formula $M^B(ER)_3$, where $M^B$ is a metal selected from the group of: In, Ga or Al; E is S or Se, and R represents an alkyl, aryl, heteroaryl, alkenyl, amide or silyl moiety. Organic substances such as aliphatic and aromatic hydrocarbons as well as siloxanes, cyclosiloxanes, silicone fluids, acetonitrile, esters and ethers are used as ink solvents. The ink is admixed with compounds with the molecular formula: $M^{alk}M^B(ER)_4$ or with the formula: $M^{alk}(ER)$ where $M^{alk}$ is: Li, Na or K, and R is an alkyl or aryl moiety. Other ink ingredients are surfactants, dispersants and emulsifiers, anti-foaming agents, viscosity modifiers, antioxidants and pro-adhesive agents. Depending on the composition, the ink is in a form of a suspension or solution, prepared by mixing all the ingredients. The ink acts as a photovoltaic layer and is applied onto the substrate by printing. In order to solidify the coating applied, the ink is dried by evaporation of the solvent.

Furthermore, perovskites are known materials used to obtain photovoltaic cells. Perovskites are hybrid organic-inorganic compounds with a general formula $ABX_3$, wherein, typically in solar cells, A is an organic methylammonium cation $(CH_3NH_3^+)$ whose presence enhances the solubility of the material, so that perovskite is suitable for thin layer application, B is an inorganic cation such as lead cation $(Pb^{2+})$, and the anion X is selected from the halogen group, typically being an anion of iodide $(I^-)$, bromide $(Br^-)$ or chloride $(Cl^-)$. Perovskites are produced in a form of films, i.e. thin coatings, which constitute the photoactive layer of a photovoltaic cell, wherein in cells with the standard architecture, the perovskite layer is located between a layer of p-type conductive material and a layer of n-type conductive material, which are typically covered with suitable electrodes, including one electrode allowing the transmission of sunlight photons.

Perovskite thin films intended for photoactive layers of photovoltaic cells are prepared from perovskite-forming compositions, which are colloidal solutions containing perovskite precursors, i.e. substrates for the synthesis of a particular perovskite, constituting the dispersed phase, wherein the colloid contains a suitable liquid as the dispersion medium, usually an organic solvent.

Two-component perovskite-forming compositions are also known that contain two physically separated components, which, after mixing, react to produce perovskite.

In the perovskite-forming compositions constituting colloidal solutions, the colloidal particles take a form of coordination complexes, typically represented by the structure of lead polyhalides between organic and inorganic components, which structure may be adjusted by changing the degree of coordination of the complex, which allows a formation of a perovskite layer, in a form of a thin film with predetermined film coverage parameters and morphology of the perovskite structure obtained.

There are also known perovskite-forming compositions in a form of inks, containing at least one perovskite precursor, in which the mechanism of curing, i.e. of forming a photoactive coating, comprises the synthesis of perovskite from the perovskite precursors contained in the composition.

An international patent application WO2016088019 discloses a film-forming composition containing at least two perovskite precursors, for example: $CH_3NH_3I$ and $PbI_2$ or $NH_2CH=NH_2I$ and $PbI_2$ or CsI and $SnO_2$. This composition may take a form of a powder or ink and may contain as a solvent, dimethylformamide (DMF) or isopropanol (IPA) as well as additives including thickening agents such as glycerol or d-sorbitol, and crystallisation retardants such as dimethylsulphoxide (DMSO). The method for curing this composition, on a selected substrate, in order to form a photoactive layer consists in applying a layer of said composition having an appropriate thickness onto the substrate and curing the composition consisting in synthesising suitable perovskites from their precursors, evaporating the solvent, if present in the composition. According to WO2016088019, depending on the form and ingredients of the film-forming composition, the film-forming composition may be applied onto the substrate using the spin-coating technique, printing and heating of the applied layer or applying a coating from the gaseous phase, including dual source evaporation, or using the ablation technique, or printing, including in particular ink-jet printing, as well as spraying, blade-coating, meniscus-coating, slot die coating, or dip coating. The resulting photoactive layer features good absorption of photons, whereas the prepared photovoltaic cells comprising the perovskite film obtained by curing the film-forming composition exhibit good efficiency.

Moreover, a scientific publication by Zhengguo Xiao et al. "*Unraveling the hidden function of a stabilizer in a precursor in improving hybrid perovskite film morphology for high efficiency solar cells*", Energy & Environmental Science, DOI: 10.1039/c6ee00183a, publication date 28 Jan. 2016 describes the synthesis of organometallic alkyl halides containing three atoms of the respective halogen: "OPT" (organometal trihalide perovskite). The publication describes the role of phosphoric acid (I) also referred to as phosphinic acid: $H_3PO_2$ in stabilising hydrogen iodide: HI is necessary for the synthesis of the perovskite precursor from the OPT group—methylammonium iodide (MAI—MethylAmmonium Iodide). Indeed, the presence of phosphoric acid (I): $H_3PO_2$ as the stabiliser of hydrogen iodide HI during the MAI synthesis effects the contamination of the reaction product with methylammonium hypophosphite: MAH2PO$_2$, which is due to H$_3$PO$_2$ reacting with methylamine (MA). Said contamination induces a substantial decrease of the crystallization reaction rate, that is to say of the synthesis of perovskite from MAI contaminated with MAH$_2$PO$_2$, and PbI$_2$ (lead iodide) due to the formation of an intermediate phase: Pb(H$_2$PO$_2$)$_2$, resulting in a highly homogeneous and smooth perovskite layer with large grains being formed. The synthesis of perovskites using MAI purified from MAH$_2$PO$_2$ by way of recrystallization, in turn, yields coarse-grained heterogeneous perovskite films, which demonstrates that the contamination with MAH$_2$PO$_2$ promotes the synthesis of perovskites. The authors of the publication suggested using Pb(H$_2$PO$_2$)$_2$ as nucleation centres for perovskite crystals.

A scientific publication by Wei Zhang et al.: "*Enhanced optoelectronic quality of perovskite thin films with hypophosphorous acid for planar heterojunction solar cells*", NATURE COMMUNICATIONS, DOI: 10.1038/ncomms10030, published on: 30 Nov. 2015, describes perovskite semiconductors such as CH$_3$NH$_3$PbI$_3$. The authors of the publication note the addition of phosphoric acid (I) (HPA) in the solution of perovskite is precursor, which significantly improves the quality of the perovskite film obtained due to HPA reducing the oxidized I$_2$ (molecular iodine) to I$^-$ (iodide anion), which improves the stoichiometry of the perovskite crystal obtained.

Another scientific publication by Wei Zhang et al.: "*Ultrasmooth organic-inorganic perovskite thin-film formation and crystallization for efficient planar heterojunction solar cells*", NATURE COMMUNICATIONS, DOI: 10.1038/ncomms7142, published on: 30 Feb. 2015, describes the role of anions in the synthesis of perovskites in solutions and how they affect the growth of perovskite crystals, and consequently the production and quality of a perovskite film. The authors of the publication used lead acetate (Pb(OAc)$_2$) instead of conventionally used lead chloride or lead iodide (PbCl$_2$, PbI$_2$), which resulted in a faster growth of perovskite crystals and smoother surface of the perovskite film. Also the heating time, during the preparation of perovskite: CH$_3$NH$_3$PbI$_3$ with precursors: Pb(OAc)$_2$ and MAI, is shorter, which is due to facilitated removal of excess CH$_3$NH$_3$OAc from the mixture.

According to the aforementioned publications, not only the concentration of perovskite precursors in the perovskite-forming composition, but all the above-mentioned methods for preparing and purifying perovskite precursors for the perovskite-forming composition in a form of a colloidal solution, substantially affects the quality and morphology of the obtained perovskite film crystals prepared using a particular composition.

Thus, the methods for obtaining perovskite precursors, i.e. raw materials for the synthesis of perovskites, are continuously modified so as to obtain compounds with an appropriate degree of purity in order to use these compounds for preparing perovskite-forming compositions for fine perovskite coatings exhibiting appropriate morphology and quality of crystals, and, consequently, increasingly superior properties of photovoltaic cells produced using such coatings as photosensitive elements.

Therefore, it would be expedient to develop a method for the synthesis of a perovskite precursor, as well as a perovskite composition containing said precursor, which would enable preparation of perovskite coatings showing improved morphology and quality of perovskite crystals.

There is disclosed a method for obtaining a salt with a general formula: R$_x$NI, wherein: R$_x$N is an organic cation (R$_x$N$^+$), R represents substituents (R—) independently selected from a group consisting of organic substituents: R$^1$—, R$^2$—, R$^3$— and hydrogen (H—), x is a number of the substituents R— directly linked with the nitrogen (N) atom in the organic cation R$_x$N$^+$, wherein x is 3 or 4, I is an iodide anion (I$^-$). The method comprises: preparing a reaction mixture comprising the steps of: synthesizing hydrogen iodide (HI) in situ by mixing molecular iodine (I$_2$) with formic acid (COOH) in a molar ratio of molecular iodine (I$_2$): formic acid (COOH) of no less than 1.01:1, in a solvent medium, introducing into the solvent medium a compound being a donor of organic cation R$_x$N$^+$ in an amount providing the molar ratio of the donor of organic cation R$_x$N$^+$: molecular iodine (I$_2$) of no less than 1.01:1, and maintaining the reaction mixture at a temperature of not less than 20° C. for the time necessary to obtain the reaction product being the salt with the general formula R$_x$NI.

Preferably, the donor of organic cation R$_x$N$^+$ contains as the organic substituents: R$^1$—, R$^2$— and optionally R$^3$— moieties independently selected from the group consisting of: straight chain or branched chain alkyl substituents containing 1 to 8 carbon atoms in the substituent molecule, optionally containing at least one heteroatom substituting the carbon atom or hydrogen atom in the substituent molecule, wherein the heteroatom is selected from the group consisting of: silicon, oxygen, nitrogen, sulphur, iodine, chlorine and bromine.

Preferably, molecular iodine (I$_2$) is mixed with formic acid (HCOOH) at the molar ratio: molecular iodine (I$_2$): formic acid (COOH) of 1.01:1 to 1.1:1, and the donor of organic cation R$_x$N$^+$ is introduced to the solvent medium in the amount providing the molar ratio of the donor of organic cation R$_x$N$^+$: molecular iodine (I$_2$) of 1.01:1 to 1.50:1.

Preferably, molecular iodine (I$_2$) is mixed with formic acid (HCOOH) at the molar ratio of iodine (I$_2$): formic acid (COOH) of 1.01:1.

Preferably, the reaction mixture is heated to a temperature in the range from 20 to 80° C.

Preferably, the donor of organic cation R$_x$N$^+$ is introduced to the solvent medium following the synthesis in situ of hydrogen iodide (HI).

Preferably, amine is used as the donor of organic cation R$_x$N$^+$, and the obtained salt (R$_x$NI) contains the organic cation (R$_x$N$^+$) selected from the group consisting of: alkylammonium cations (R(H$_3$)N$^+$), dialkylammonium cations R$_2$(H$_2$)N$^+$, and trialkylammonium cations (R$_3$(H)N$^+$).

Preferably, primary alkylamine with the general formula RNH$_2$ is used as the donor of organic cation R$_x$N$^+$, and the obtained salt: alkyl ammonium iodide has the general formula of R(H$_3$)NI, where the substituent R represents an alkyl moiety containing 1 to 8 carbon atoms.

Preferably, methylamine is used as the donor of organic cation R$_x$N$^+$, and methylammonium iodide (MAI) is obtained as the salt.

Preferably, octylamine is used as the donor of organic cation R$_x$N$^+$, and octylammonium iodide (OAI) is obtained as the salt.

Preferably, an amidine salt is used as the donor of organic cation R$_x$N$^+$ and amidinium iodide (R$_2$N—(R$^3$)C=N(H$_2$)I) is obtained as the salt.

Preferably, formamidine acetate is used as the donor of organic cation R$_x$N$^+$ and formamidinium iodide (FAI) (H$_2$N—C(H)=N(H$_2$)I) is obtained as the salt.

Preferably, the solvent medium comprises at least one compound selected from the group consisting of: methanol, ethanol, absolute ethanol, isopropanol, dioxane, tetrahydrofuran (THF) and dimethylformamide (DMF).

Preferably, the solvent medium is water.

Preferably, preparing the reaction mixture further comprises the step of introducing, into the solvent medium, a catalyst being a salt with the general formula $R_xNI$.

Preferably, the catalyst is a compound identical to the salt $R_xNI$ being the reaction product.

Preferably, the catalyst is obtained by the method according to the present disclosure.

Preferably, the catalyst is introduced at a molar ratio of catalyst: molecular iodine ($I_2$) ranging from 0.01:1 to 0.03:1.

Further, there is disclosed a use of a salt with the general formula: $R_xNI$ prepared using the method according to the present disclosure, as the substrate in a synthesis of perovskites.

Furthermore, there is disclosed a perovskite-forming composition which comprises the salt with the general formula: $R_xNI$ obtained using the method according to the present disclosure.

Preferably, the composition comprises the salt with the general formula: $R_xNI$ selected from the group consisting of: methylammonium iodide (MAI), ethylammonium iodide, propylammonium iodide, butylammonium iodide, pentylammonium iodide, hexylammonium iodide, heptylammonium iodide, octylammonium iodide (OAI) and formamidinium iodide (FAI).

Preferably, the composition further comprises at least one lead salt and at least one solvent.

Preferably, the composition further comprises methylammonium dihydrogen phosphate (I) $CH_3NH_3H_2PO_2$.

Preferably, the composition comprises the following compounds: methyl ammonium iodide (MAI), anhydrous lead (II) acetate $(CH_3COO)_2Pb$ and lead (II) chloride $PbCl_2$ in the amounts effective for the synthesis of perovskite from said compounds, as well as dimethylformamide (DMF) as a solvent and methyl ammonium dihydrogen phosphate (I) $CH_3NH_3H_2PO_2$ in the amount of 0.3% by weight with respect to the weight of methylammonium iodide (MAI) contained in the composition.

Preferably, the composition comprises formamidinium iodide (FAI), methylammonium bromide $CH_3NH_3Br$, lead (II) iodide $PbI_2$ and caesium iodide (CsI), in the amounts effective for the synthesis of perovskite from said compounds.

There is further disclosed a photovoltaic cell compring a perovskite layer prepared using the salt with the general formula: $R_xNI$, that is obtained using the method according to the present disclosure.

Preferably, the cell comprises a perovskite layer obtained from the perovskite-forming composition comprising ingredients as described above.

The object of the invention is shown in exemplary embodiments in the drawing where:

FIG. 1 is a schematic representation of the synthesis reactions of organic iodide ($R_xNI$) using the method according to the disclosure;

FIG. 2 is a schematic representation of the synthesis reactions of methylammonium iodide (MAI) using the method according to the disclosure;

FIG. 3 is a schematic representation of the synthesis reactions of octylammonium iodide (OAI) using the method according to the disclosure;

FIG. 4 is a schematic representation of the synthesis reactions of formamidinium iodide (FAI) using the method according to the disclosure;

FIG. 5 is a schematic representation of structural and semi-structural formulae of exemplary organic iodides obtained using the method according to the disclosure;

Figure 8A:
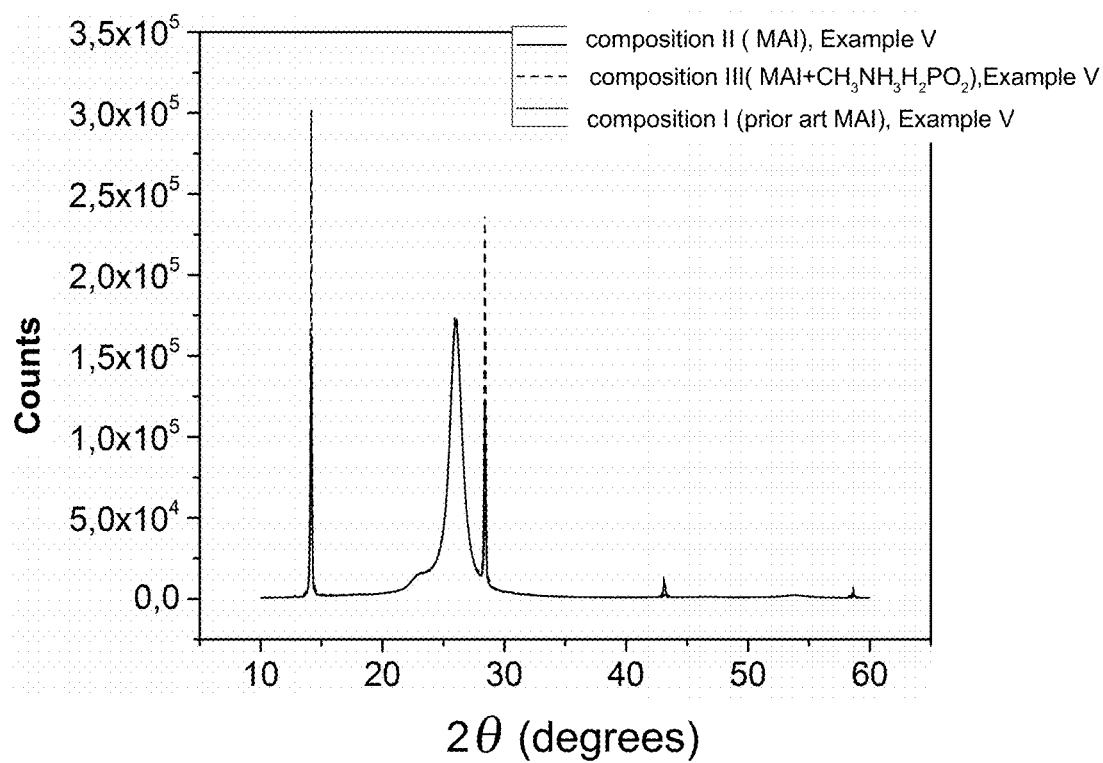
Figure 8B:
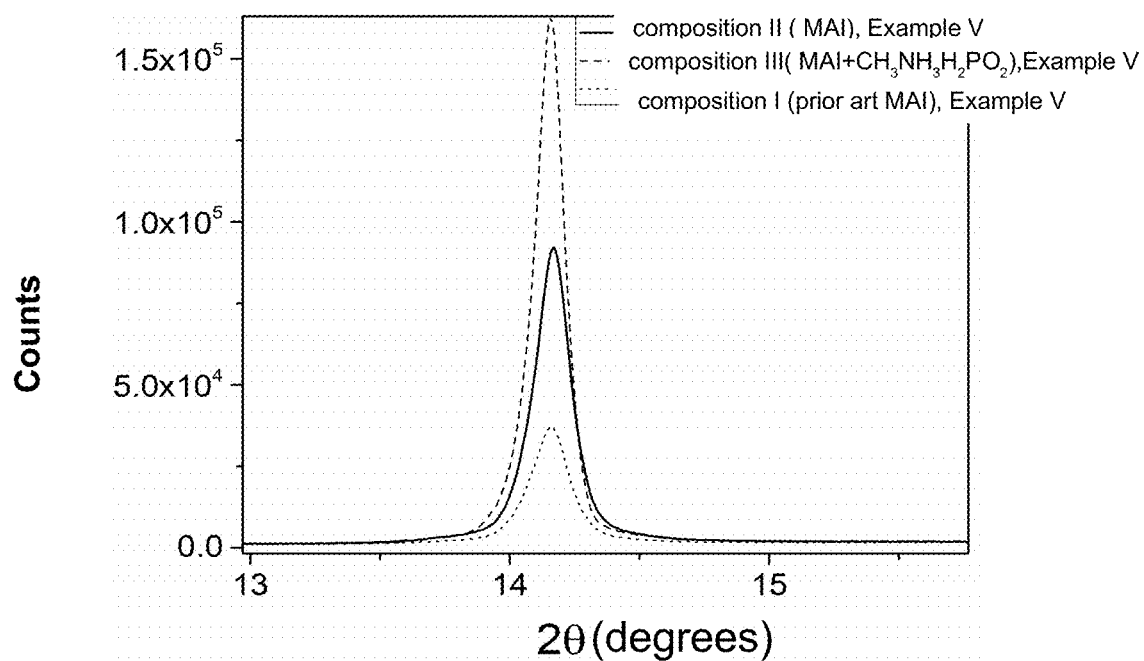
Figure 8C:
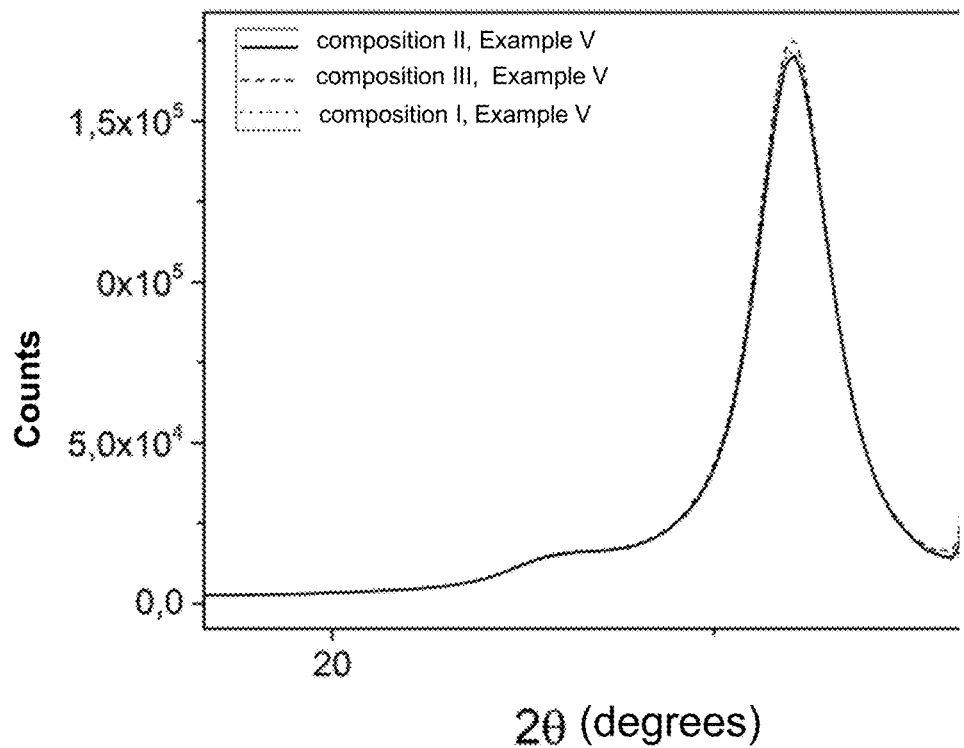
Figure 9A:
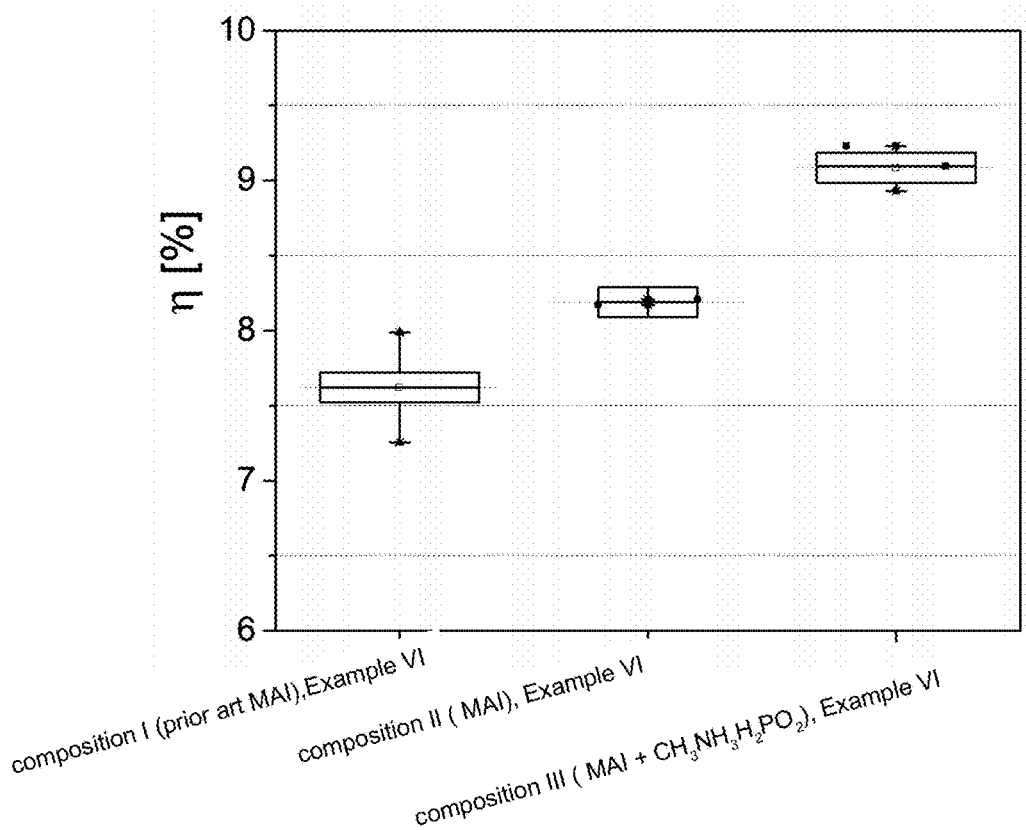
Figure 9B:
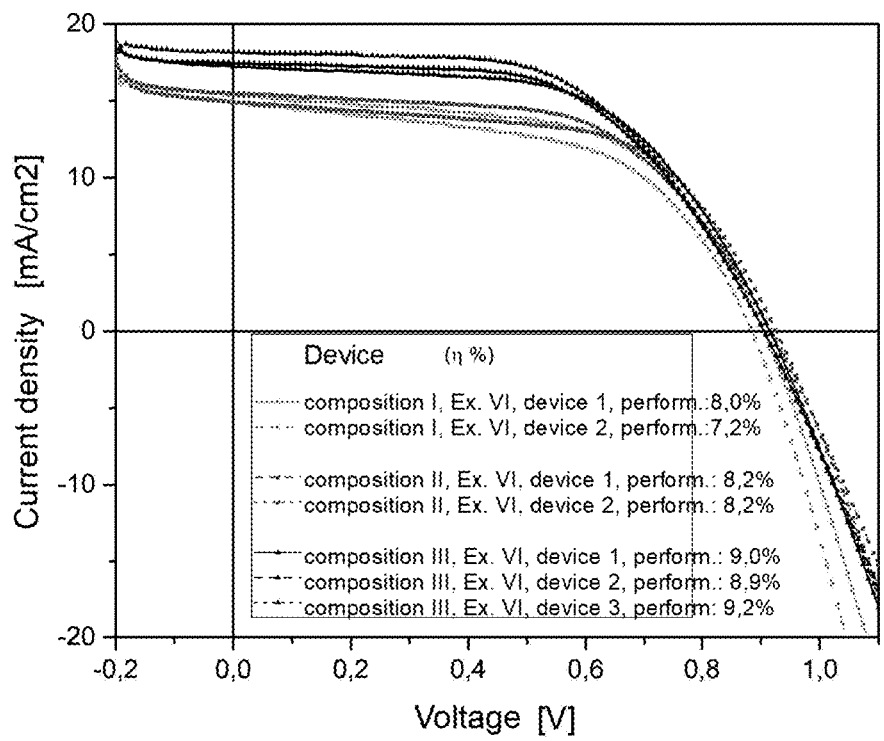
Figure 10:
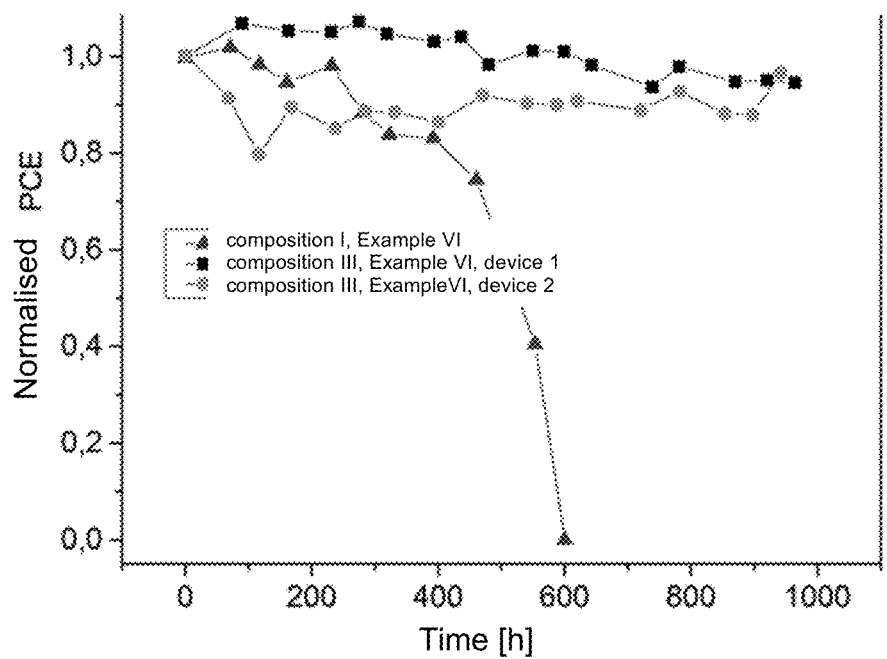
Figure 11A:
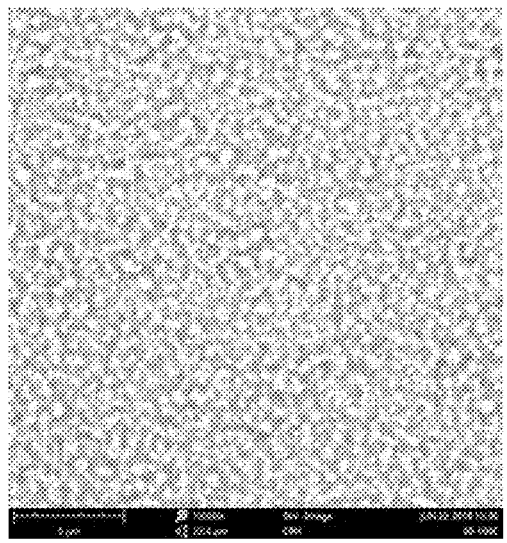
Figure 11B:
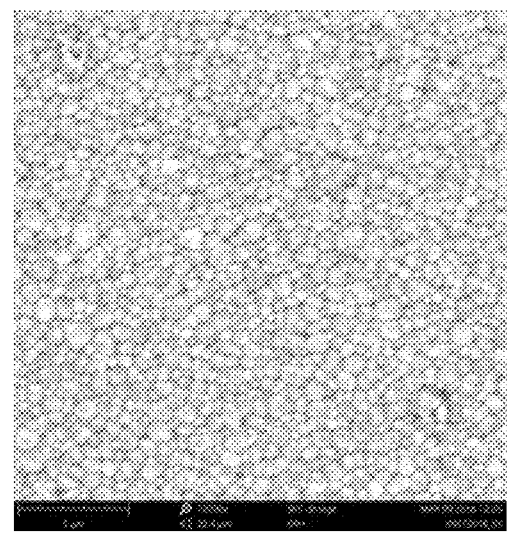
Figure 12A:
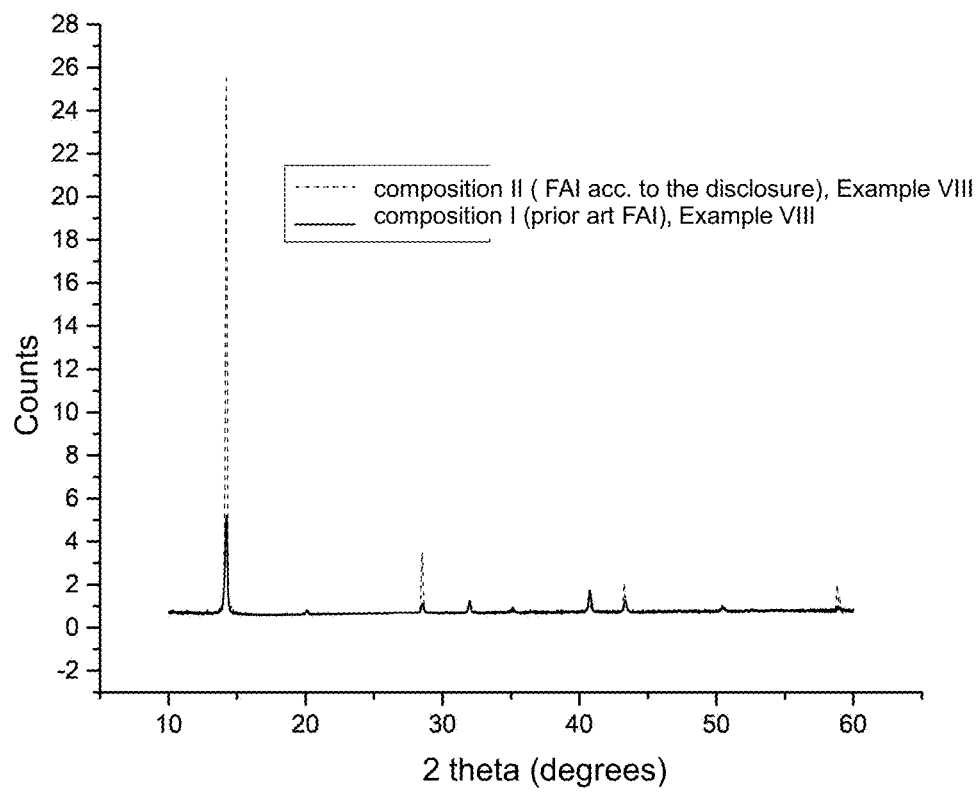
Figure 12B:
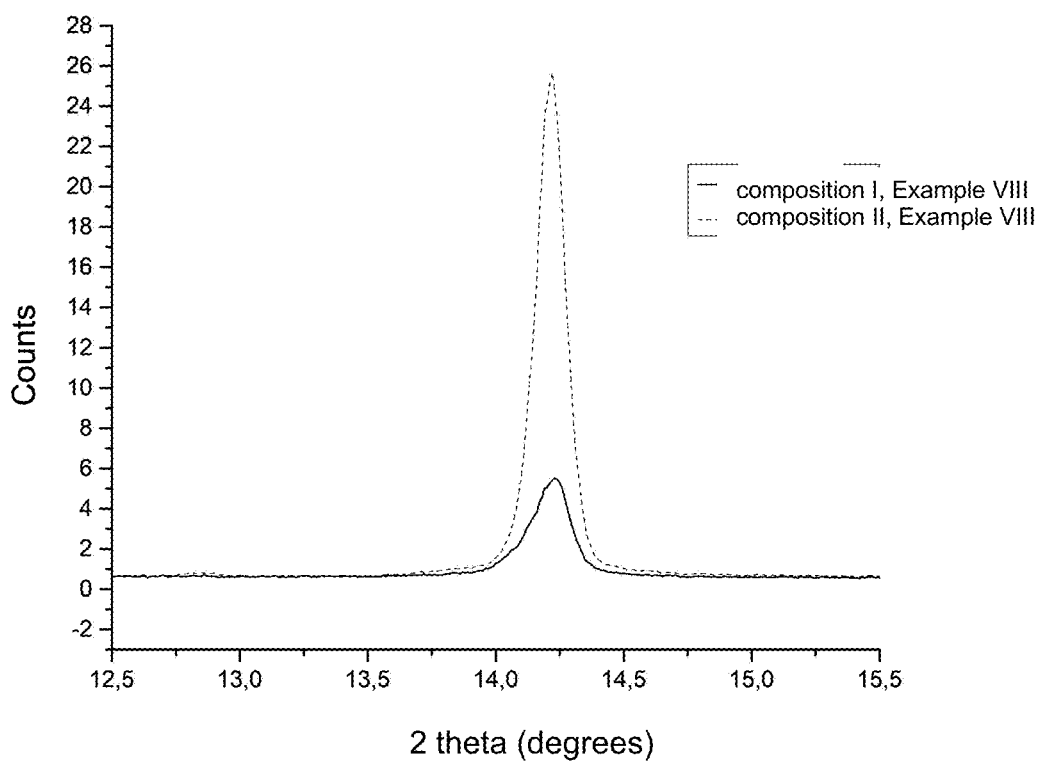
Figure 13:
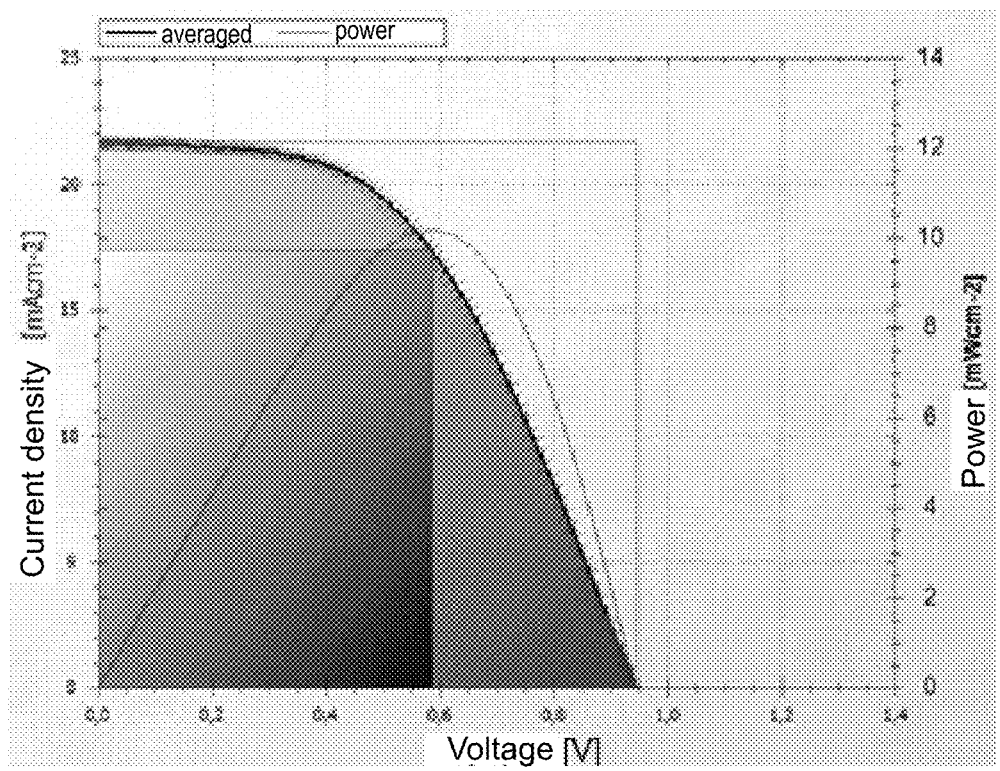
Figure 14A:
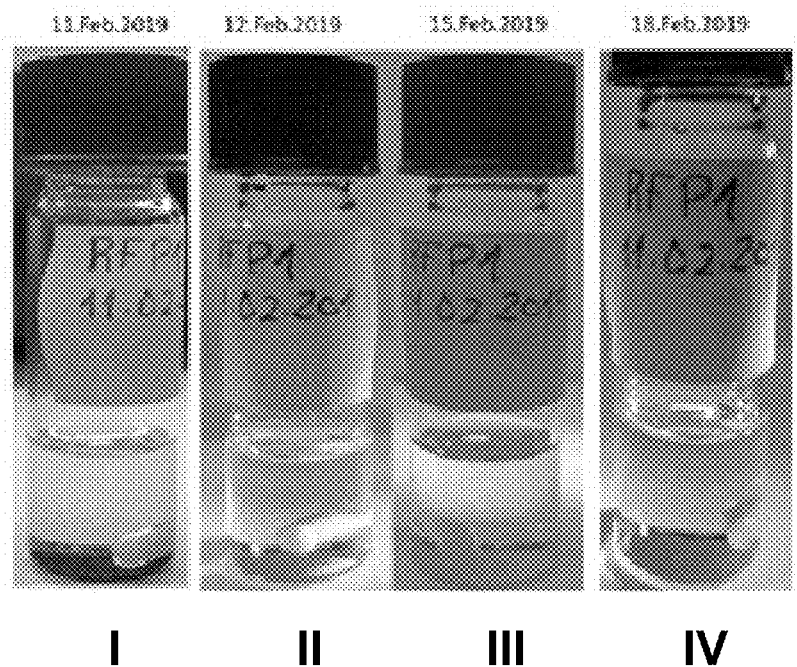
Figure 14B:
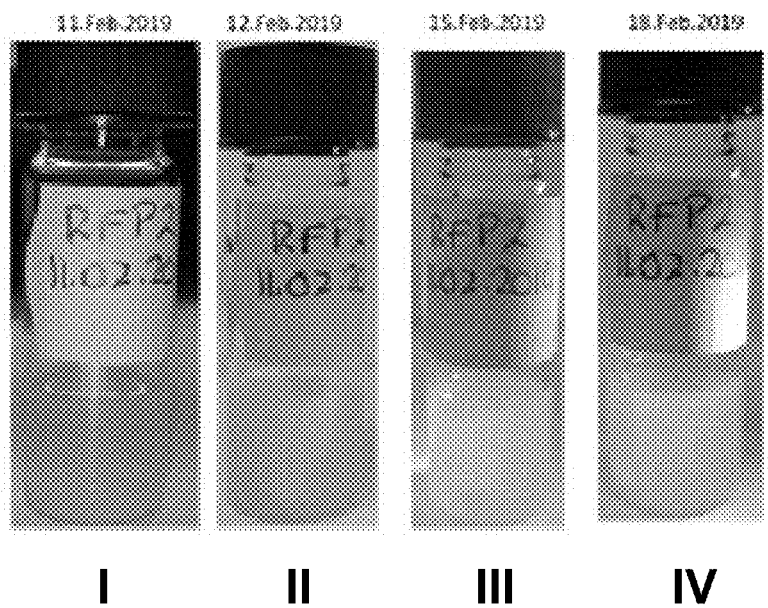
Figure 14C:
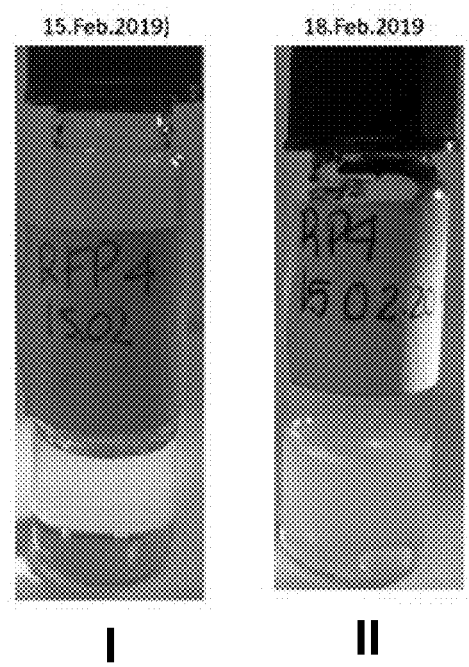
Figure 14D:
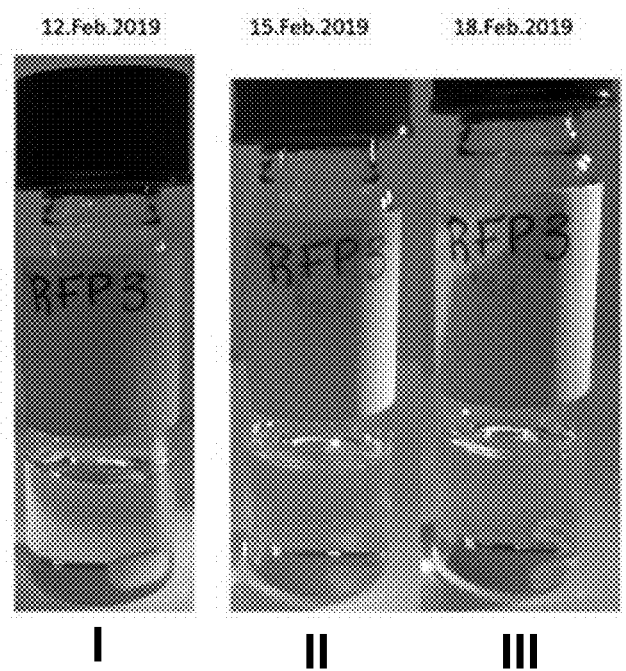

FIG. 6 presents examples of synthesis of perovskites from iodide obtained using the method according to the disclosure;

FIG. 7 shows SEM images of perovskite coatings in a form of thin films on PEDOT/PET/ITO substrates;

FIG. 8A shows imposed X-ray diffractograms of $CH_3NH_3PbI_3$ obtained with: MAI synthesised using the method according to the invention, MAI synthesised using the method according to the invention with added $MAH_2PO_2$, FIG. 8B shows an enlarged peak corresponding to the reflection (110) in the tetragonal plane of the perovskite phase for comparison with FIG. 8A, while FIG. 8C shows an enlarged peak (control) corresponding to the PET material;

FIG. 9A shows the results of measurement of cell efficiency ($\eta$) determining the energy conversion efficiency of a cell, depending on the type of perovskite-forming composition used for forming a perovskite layer of the cell;

FIG. 9B shows the test results presenting current density-voltage dependence for selected perovskite cells;

FIG. 10 shows the results of the ageing tests carried out for selected cells: ageing at the maximum power point, under sunlight of: 0.8, in an inert atmosphere and temperature of 32° C.;

FIG. 11A shows a SEM image of a perovskite coating prepared with Composition I, Example VIII, and FIG. 11B shows a SEM image of a perovskite coating prepared with Composition II, Example VIII;

FIG. 12A is imposed X-ray diffractograms of the network of two perovskites; and FIG. 12B shows an enlarged peak corresponding to the reflection (100) in the tetragonal plane of the perovskite phase;

FIG. 13 shows current density-voltage dependence for the prepared cell;

FIG. 14A shows images of colloids containing MAI obtained using the method according to the invention, FIG. 14B shows images of colloids of identical composition containing MAI obtained using a prior art method (commercially available MAI), FIG. 14C shows photographs of colloids of identical composition containing MAI obtained using a prior art method, and recrystallized once, FIG. 14D shows photographs of colloids of identical composition containing MAI obtained using a prior art method, and recrystallized trice.

The developed method according to the invention allows for preparing a group of chemical compounds to be used as perovskite precursors, which are salts with the general formula $R_xN$, and in the ion notation: $RxN^+I^-$, where $R_xN^+$ is an organic cation, $I^-$ is an iodide anion, and x is the number of substituents directly linked to the nitrogen atom, preferably x is from 3 to 4 (if x=3 a double bond in the organic cation exists between the nitrogen atom and the carbon atom in one R moiety).

The developed method for preparing $R_xNI$ compounds ensures improved purity of the obtained products, which in turn enable for using them as perovskite precursors in various perovskite-forming compositions, including colloidal solutions, such as inks, for producing perovskite coatings with improved morphology and quality of perovskite crystals.

The developed method of the iodide synthesis differs from the prior art methods in that the method according to the present disclosure involves the step of obtaining hydrogen iodide (HI) in situ in the reaction medium. In other words, according to the developed method, hydrogen iodide (HI) is not used as a direct substrate for the synthesis of the respective iodides. Instead, the developed method comprises the step of supplying, into the reaction medium, the substrates that are suitable for in situ hydrogen iodide (HI) synthesis.

The developed method allows for obtaining various compounds which are iodide salts with the molecular formula $R_xNI$, wherein organic cation $R_xN^+$ is selected from a group consisting of:

ammonium cations with the general formula: $R_4N^+$ (x=4), including alkylammonium cations: $R^1(H_3)N^+$, dialkylammonium cations: $R^1R^2(H_2)N^+$ and trialkylammonium cations: $R^1R^2R^3(H)N^+$, and ammonium cations with the general formula: $R_3N^+$ (x=3), including amidinium cations: $R^1R^2N-(R^3)C=N(H_2)^+$, and formamidinium cations: $R^1R^2N-C(H)=N(H_2)^+$, wherein moiety: R— is selected from the group: H—, $R^1$—, $R^2$— and $R^3$—, in accordance with the general formulas of cations as indicated above. The substituents R—, $R^1$—, $R^2$—, $R^3$— may be the same or different moieties selected from a group consisting of: hydrogen (H—), straight chain and/or branched aliphatic hydrocarbons ($C_yH_z$—), alicyclic hydrocarbons, including saturated hydrocarbons and/or containing an unsaturated bond or bonds, and aromatic hydrocarbons. Preferably, every substituent: $R-R^1$—, $R^2$—, $R^3$— of organic cation ($R_xN^+$), other than (H—) may contain 1 to 8 carbon atoms in the molecule, i.e. for at least one substituent: $R-R^1$—, $R^2$—, $R^3$— with the general formula $C_yH_z$—, y may be: 1÷8. Also, at least one substituent: $R^1$—, $R^2$—, $R^3$— of the organic cation may have at least one atom of carbon or hydrogen substituted with another atom, for example: silicon, oxygen, nitrogen, sulphur, iodine, chlorine or bromine.

For example, the developed method may be used to obtain iodide salts ($R_xNI$), wherein the organic cation ($R_xN^+$), for x=4, is methylammonium $CH_3(H_3)N^+$, ethylammonium $CH_3CH_2(H_3)N^+$, propylammonium $C_3H_7(H_3)N^+$, butylammonium $C_4H_9(H_3)N^+$, pentylammonium $H_3C_5H_{11}N^+$, hexylammonium $H_3C_6H_{13}N^+$, heptylammonium $C_7H_{15}(H_3)N^+$ or octylammonium $C_8H_{17}(H_3)N^+$ cation, and for x=3, is formamidinium $(H_2N-HC=NH_2)^+$, or guanidinium $(H_2N)_2-C=NH_2)^+$ cation.

For greater clarity, examples of iodides salts, which may be obtained using the inventive method, are shown, in a form of structural and semi-structural formulae, in FIG. 5, wherein formulae I and II are general iodide formulae, for which formula I represents a salt with the general formula $R_4NI$ (i.e. x=4), formula II represents salt $R_3NI$ (i.e. x=3), and formulae: III, IV and V, respectively provide detailed examples of the compounds that may be obtained using the developed method, wherein: formula III represents methylammonium iodide (MAI), formula IV represents octylammonium iodide (OAI) and formula V represents formamidinium iodide (FAI).

Thus, the developed method enables one to obtain iodide salts $R_4NI$ (FIG. 5, formula I), such as: methylammonium iodide (MAI), dimethylammonium iodide, propylammonium iodide, methylethylammonium iodide, butylammonium iodide, pentylammonium iodide, hexylammonium iodide, heptylammonium iodide, octylammonium iodide (OAI), as well as iodide salts with the general formula $R_3NI$ (FIG. 5, formula II), such as formamidinium iodide (FAI) or guanidinium iodide (GAI).

FIGS. 1-4 are schematic representation of the reactions occurring during the synthesis according to the developed method, with FIGS. 1A, 2A, 3A and 4A showing the synthesis without the use of a catalyst, while FIGS. 1B, 2B, 3B, and 4B show synthesis with the use of catalyst, being an option. The developed method for preparing iodide salts ($R_xNI$) comprises steps in which, molecular iodine $I_2$ is supplied to a reaction medium in excess with respect to formic acid (HCOOH), and in deficit with respect to a donor of organic cation ($R_xN^+$), formic acid (HCOOH) is supplied in the amount as indicated above, with respect to molecular iodine ($I_2$), in order to produce hydrogen iodine (HI) in situ (in the reaction medium), with the release of carbon dioxide ($CO_2$) being a by-product of HI synthesis, and a compound which is the donor of organic cation $R_xN^+$ is supplied to the reaction medium, in the amount as indicated above, and therefore corresponding to the amount of molecular iodine ($I_2$), and the donor of organic cation donor $R_xN^+$ reacts with hydrogen iodine (HI) synthesised in situ, in the reaction medium, to produce a respective $R_xNI$ salt.

Depending on the target synthesis product, various organic compounds may be used as the donors of organic cation $R_xN^+$ i.e. the compounds that are capable of dissociation in the reaction medium to form a respective organic cation: $R_xN^+$, i.e. a cation selected from the group: $R_4N^+$ and $R_3N^+$.

Preferably, compounds whose dissociation does not involve introducing additional, and difficult to remove, contaminations to the reaction medium are used as the donors of organic cation $R_xN^+$.

Examples of Compounds to be Used as the Donor of Organic Cation $R_xN^+$ According to the Developed Method for Preparing $R_xNI$ Salts:

For example, amines, preferably primary amines, and preferably containing 1 to 8 carbon atoms in the molecule, such as methylamine ($CH_3NH_2$) to obtain methylammonium iodide ($CH_3NH_3I$), ethylamine ($C_2H_5NH_2$) to obtain ethylammonium iodide ($C_2H_5NH_3I$) or octylamine ($C_8H_{17}NH_2$) to obtain octylammonium iodide ($C_8H_{17}NH_3I$), may be used as the donor of organic cation $R_4N^+$ (i.e. x=4). The respective amines will therefore dissociate, yielding the respective organic cation $R_4N^+$ being the substrate for salt synthesis.

Furthermore, amidine acetates, such as formamidine acetate, may be used as the donor of organic cation $R_3N^+$ (i.e. x=3): (with the formula in ion notation: $[(HC(NH_2)_2]^+$ $[CH_3COO]^-$), since these compounds readily dissolve under reaction conditions and dissociate to the respective organic cations $R_3N^+$ and acetate anion, which, in the course of the reaction, is converted to acetic acid and which, due to its low boiling point, can be evaporated from the solution and thus easily removed from the post-reaction mixture.

The above-mentioned selection of a compound serving as the donor of organic cation provides high purity of synthesis product, i.e. a salt containing an iodide anion and an organic cation, so that the quality of perovskite coatings made with the salt $R_xNI$ prepared using the developed method is improved.

Depending on the solubility of the donor of organic cation $R_xN^+$ used, the reaction may be carried out in polar or apolar medium, with various solvents providing good solubility of molecular iodine ($I_2$) (reactions presented in FIGS. 1A, 2A, 3A and 4A) or iodine in ionised form: $I_3^-$ (reactions presented in FIGS. 1B, 2B, 3B and 4B) as well as providing good solubility of the donor of organic cation $R_xN^+$ used. Moreover, the solvent should preferably allow the reaction to be carried out at a temperature above 50° C., so that for example the solvent should have a boiling point of over 50° C., and, more preferably, a boiling point between 50 and 150° C. A solvent with a boiling point above 150° C. could be difficult to remove when cleaning the reaction product, thus, such the solvent may constitute an undesired contamination, and therefore is less preferred for use.

For example, in the embodiment of the disclosure with methylamine used as the donor of organic cation, the reaction can be carried out in a solvent such as water, methanol, ethanol, absolute ethanol (at a concentration of 99.8%, for example, obtained by distillation with added benzene; the contamination of the solvent with a small amount of benzene does not adversely affect the final purity of the product, since it may be removed in the course of purification), isopropanol, a mixture of suitable alcohol with water, dioxane, tetrahydrofuran (THF), wherein the reaction is preferably carried out using absolute ethanol as the solvent, since absolute ethanol provides relatively high solubility of substrates including molecular iodine and the donors of organic cation, including methylamine. Furthermore ethanol has a boiling point of 78° C., thus allowing the reaction to be carried out at preferred temperature of over 50° C. Moreover, absolute ethanol is easily removable in the course of the purification of the reaction product.

Together with the increase of the number of carbon atoms in the molecule of the donor of organic cation, the polar character of the molecule weakens in favor of non-polar character of the molecule. This imposes using, instead of water, solvents such as methanol, ethanol, isopropanol, absolute ethanol, dioxane, tetrahydrofuran (THF).

For example, where octylamine or formamidine acetate is used as the donor of organic cation, ethanol may be used as the solvent.

Introduction of the donor of organic cation in the course of preparation of the reaction mixture, is preferably accomplished at the temperature from the range of 0 to 30° C. For example, the addition of the donor of organic cation may be accomplished at room temperature, since the reaction triggered by such the addition is exothermic by nature. After adding the compound being the donor of organic cation, the reaction mixture is heated preferably to the temperature exceeding 50° C. This ensures an increase in the reaction rate. In such temperature conditions the reaction can be carried out within a relatively short period of time, e.g., less than 2 hours, with satisfactory product yield.

FIG. 1A, 2A, 3A, 4A schematically represent the respective reaction stages of iodides salts synthesis, according to the developed method, in a form of stoichiometric equations, wherein FIG. 1A is a general representation of the reaction of $R_xNI$ iodide synthesis, while FIG. 2A presents synthesis of methylammonium iodide (MAI), FIG. 3A presents synthesis of octylammonium iodide (OAI), while FIG. 4A presents synthesis of formamidinium iodide (FAI). In FIGS. 1A, 2A, 3A, 4A, reactions marked with reference numbers 1 and 2 represent the individual synthesis steps, including intermediate products, while the reaction marked with reference number 3 is a summary of reactions 1 and 2.

As illustrated in FIG. 1A-4A, in the first synthesis step (reaction 1), formic acid (HCOOH) reacts with molecular iodine ($I_2$) to form hydrogen iodide ($H^+I^-$) in situ and by-product carbon dioxide ($CO_2$) which is released. The formed hydrogen iodide constitutes the source of iodide anions. The iodide ions ($I^-$) then react (reaction 2) with the compound being the donor of organic cations, yielding the reaction product: iodide of the respective organic cation $R_xNI$.

The reaction is carried out with an excess of iodine ($I_2$) with respect to formic acid (HCOOH), wherein, preferably, in the reaction there is used an excess of iodine at a molar ratio from 1.01 ($I_2$): 1.0 (HCOOH) to 2.0 ($I_2$): 1.0 (HCOOH) and more preferably, molecular iodine ($II_2$) is used in excess at a molar ratio with respect to formic acid of 1.01 ($I_2$): 1.0 (HCOOH) to 1.10 ($I_2$): 1 (HCOOH), and most preferably at a molar ratio of 1.05 ($I_2$): 1 (HCOOH).

The excess of molecular iodine with respect to formic acid in the reaction medium provides the synthesis of respective iodide salt with improved (superior) purity.

Even a small excess of iodine ($I_2$) with respect to formic acid (HCOOH), and more preferably an excess of $I_2$ with respect to HCOOH in the range indicated above, prevents the formation in the reaction mixture of by-products being formates of respective organic cations ($[R_xN^+]$ $[HCOO^-]$), whose donors are added to the reaction mixture. Such salts ($[R_xN^+]$ $[HCOO^-]$), are difficult to separate from the reaction product, and in some cases (of specific salts and specific products) it is impossible without using costly specialised purification methods. Therefore, it is advantageous to use molecular iodine in appropriate excess.

The use of molecular iodine in excess with respect to formic acid always improves the purity of the obtained product by limiting the formation of hard-to-remove by-products ($[R_xN^+]$ $[HCOO^-]$), wherein the most advantageous molecular iodine excess, providing a substantial reduction in the formation of reaction by-products of hard-to-remove salts ($[R_xN^+]$ $[HCOO^-]$) is from 1.01 to 1.10 mole $I_2$ per 1 mole HCOOH.

Further, in order to remove iodine present in the post-reaction mixture, the product needs to be purified, and if an excess of iodine used is higher than indicated, the purification procedure may need to be repeated (recrystallization), which generates additional costs due to the use of additional solvents, which is also time-consuming.

Consequently, in order to prevent contamination of the final product with both the excess of unreacted iodine and reaction by-products in a form of acetic acid salts ($[R_xN^+]$ $[HCOO^-]$), a preferred excess of iodine which may be used is 1.01 mole $I_2$ per 1 mole HCOOH, such value provides optimally high purity of the final product.

Moreover, the reaction is carried out in an excess of the donor of organic cation ($R_xN^+$) (examples of which are indicated above) with respect to molecular iodine ($I_2$), wherein the most preferred excess of the donor of organic cation with respect to molecular iodine is in the range of 1.01 to 1.50 mole of the donor of organic cation for each 1 mole of molecular iodine ($I_2$). The use of an excess of the donor of organic cation provides the advantages described below. Inter alia, the excess of organic cation ($R_xN^+$) with respect to molecular iodine ensures complete reaction of the hydrogen iodide (HI), obtained in-situ, with the organic cation. If the obtained HI remained in the reaction environment, resulting from a molar deficit of the donor of organic cation, at the end of the reaction, this remained acid HI might undergo oxidation to iodine oxoacids such as: HIO, $HIO_2$, $HIO_3$ and $HIO_4$, so that by-products (in a form of respective salts) might be formed through anion-exchange reactions between the iodine oxoacids and the reaction product. Such salts would be very difficult to separate from the product, resulting in lower purity of the product (the respective iodide salt). Therefore, in order to prevent an excess of hydrogen iodide (HI) prepared in situ with respect to the donor of organic cation an excess of the donor of organic cation ($R_xN^+$) is used, and this prevents the contamination of the reaction product, as explained above. In other words, the excess of organic cation ($R_xN^+$) with respect to the amount of molecular iodine ($I_2$) added to the reaction medium ensures improved purity of the product obtained. Moreover, for the embodiments according to the present disclosure, in which the donor of organic cation ($R_xN^+$) is in a gas or liquid state, at the given reaction conditions, unreacted excess of said compound may be easily separated from the reaction product using commonly known purification techniques.

An additional advantage of providing an excess of the donor of organic cation ($R_xN^+$), at the preparation of the reaction mixture, is a relatively low price of the mentioned compounds (such as methylamine) comparing to the price of molecular iodine ($I_2$), which means a reduction in the cost of preparing respective iodides using the developed method.

Optionally, in order to achieve improved time efficiency, the reaction of the synthesis of the salt $R_xNI$ may be carried out with the presence of a small amount of catalyst, being a compound, preferably, identical to the $R_xNI$ iodide salt being the reaction product. Reactions with the use of respective catalyst are shown in FIG. 1B—as a general representation, and as exemplary embodiments: in FIG. 2B,—synthesis of methylammonium iodide (MAI), FIG. 3B—synthesis of octylammonium iodide (OAI), and FIG. 4B—synthesis of formamidinium iodide (FAI). Thus, for example, in order to obtain methylammonium iodide (MAI) as a product, a small (catalytic) amount of MAI is mixed with iodine ($I_2$) in the first step, as shown in FIG. 2B (reaction 1).

Thus, similar to the steps of synthesis of the respective iodides: MAI, OAI and FAI, without catalyst (FIG. 2A, 3A, 4A), FIGS. 2B, 3B and 4B: reactions 1 to 3 show the individual steps of the synthesis of the product with the catalyst, indicating the transition states and intermediate products, while reaction 4 is a summary of reactions 1-3: substrates and products.

As may be seen in FIGS. 1B, 2B and 3B, 4B, in the first step (reaction 1), the catalyst being a respective iodide salt (preferably the same as the one to be obtained) reacts with iodine ($I_2$), yielding a transition state: a three-atom iodine anion: $I_3^-$, which then (reaction 2) reacts with formic acid, yielding: a respective iodide salt, hydrogen iodide (HI) in situ and carbon dioxide. Then (reaction 3), the resulting $I^-$ iodide anions react with the organic cation donor compound $R_xN^+$ to yield the respective $R_xNI$, iodide salt, which is the reaction product.

$I_3^-$ ions, formed with the catalyst added to the reaction, feature greatly improved solubility, in polar solvents, and they react more readily with formic acid HCOOH, yielding hydrogen iodide (HI) in situ, when compared to that of molecular iodine ($I_2$), which is slightly less prone to react with formic acid with obtaining hydrogen iodide (HI) in situ. Thus, the addition of a catalyst (FIG. 1B-4B, respectively) enables a faster reaction process.

Since the formation of a transition form: a three-atom iodine anion: $I_3^-$ has an accelerating effect, the reaction with the presence of the catalyst can be carried out e.g. on an industrial or semi-technical scale, thus increasing the production capacity of said compounds.

The addition of the catalyst reduces the reaction time by approximately 60 to 180 minutes. Thus, with added catalyst, the average reaction time is 20 to 120 minutes, while without catalyst, the average reaction time is 120 to 300 minutes.

An additional advantage of using the catalyst being the same compound as the product of the reaction is improved purity of the resulting product as the catalyst and the reaction product are the same compounds, thereby the catalyst does not constitute contamination of the product. However, using as the catalyst a iodide salt, preferably $R_xNI$, which is not the same compound as the synthesised product, will also increase the reaction rate.

Preferably, the catalyst is added to the system in an amount of 0.01 to 0.03 mole per each mole of molecular iodine ($II_2$), i.e. in the molar ratio of 0.01 (mole of the catalyst): 1 (mole of $I_2$) to 0.03 (mole of the catalyst):1 (mole of $I_2$). The reaction with the presence of catalyst is carried out at a temperature ranging from 0 to 80° C.

Thus, in the MAI synthesis, MAI may be preferably used as the catalyst, in the OAI synthesis, OAI may be preferably used as the catalyst, and in the FAI synthesis, FAI may be preferably used as the catalyst.

$R_xNI$ iodides salts obtained using the developed method feature improved product purity and are suitable e.g. to be used as one of the precursor components of the respective perovskite, in perovskite-forming compositions, for example, such as perovskite inks for printing on various substrates, such as: ITO, to prepare perovskite photoactive layers in photovoltaic cells.

The use of $R_xNI$ iodides obtained using the inventive method in perovskite-forming compositions, especially those used in photovoltaics in photoactive layers, is particularly advantageous. This is because the $R_xNI$ iodides obtained, used as one of the substrates in the synthesis of perovskites, ensure the formation of a perovskite layer exhibiting improved morphology, resulting in improved photoactive properties of the resulting perovskite layer.

Preferably, the obtained products ($R_xNI$) are recrystallized to isolate them from unreacted substrates used in the synthesis.

FIG. 6 shows exemplary reactions of perovskites synthesis from the iodides $R_xNI$ prepared using the method according to the present disclosure. The obtained perovskites are suitable for use in photovoltaic cells, as photoactive layers. The reactions: 1, 2, 3, 5 and 6 present syntheses in which one of the precursors of perovskite is methylammonium iodide (MAI) prepared using the developed method, while another precursor is iodide, bromide or lead (II) chloride or tin (II) iodide, respectively. Reaction 4 represents a synthesis wherein one of the perovskite precursors is formamidinium iodide (FAI) prepared using the method according to the present disclosure, and another perovskite precursor is lead (II) iodide.

Thus, iodides prepared using the developed method can be used to obtain various perovskites, including in particular those used in photovoltaics, for photoactive layers.

The iodides obtained using the developed method, due to their high purity, are suitable to be used in perovskite-forming compositions as precursor components of perovskites (for example, in accordance with the reactions in FIG. 6) including those in a form of colloidal solutions containing, as the other perovskite precursor, the respective lead salt: lead halide: lead (II) iodide, lead (II) chloride or lead (II) bromide.

Moreover, in the course of further research, the results of which are discussed below in the embodiments of the invention, it was found that a particularly advantageous perovskite-forming composition in a form of a colloidal solution is the composition containing iodide salt obtained using the developed method and added methylammonium dihydrogen phosphate (I) $CH_3NH_3H_2PO_2$ is especially suitable, since the perovskite-forming layers obtained with this composition provide improved parameters of the photovoltaic cell obtained therewith.

EMBODIMENTS

Example I

Synthesis of Methylammonium Iodide (MAI), Using MAI as a Catalyst

In a round-bottomed flask, a portion of MAI catalyst was dissolved in ethanol, adding MAI in an amount of 0.01 mole with respect to each $I_2$ iodine mole to obtain a bright, translucent solution. Then, a whole portion of $I_2$ iodine, dark brown in colour, was added to the resulting solution in a single step to obtain a brown, non-translucent solution, which confirmed the presence of iodine ($I_2$) in the solution. After 5 minutes, this dissolved, which demonstrated that $I_3^-$ were formed in the solution (otherwise $I_2$ molecular iodine would dissolve at a much lower rate). Formic acid was then added to the resulting mixture in a single step, in molar ratio with respect to $I_2$ iodine of 0.97:1.0, and macroscopically, no changes were observed in the flask. Methylamine, a donor of suitable organic cations, was then added to the solution. Methylamine was slowly added dropwise to the solution, making a total of 2.6 moles of methylamine per each mole of $I_2$ iodine added to the solution. When adding methylamine, the formation of gas bubbles and foaming of the flask content was observed, which indicated that $CO_2$ gas was released from the reaction mixture. During the reaction, an increase in temperature was also observed, which indicates that the reaction is exothermic. Bubble formation was observed only after adding methylamine, which can be explained by the fact that the use of hydrogen iodide (HI) produced in situ significantly accelerates the reaction. After completed adding of methylamine, the brown mixture was heated for 1 hour while maintaining the temperature of the mixture at 80° C., after which the reaction was terminated. After 1 hour of heating, the mixture turned pale brown from brown; however, the colour of the mixture was not considered to be an indicator of the termination of the reaction, due to the excess of iodine used with respect to formic acid, preventing the conversion of the whole content of iodine ($I_2$) into hydrogen iodide (HI). The excess iodine used added to the reaction prevented the formation of methylammonium formate as a by-product of the reaction. The obtained product was isolated by evaporation of the solvent from the post-reaction mixture to obtain a yellow and brown powder, which was completely dissolved in boiling absolute ethyl alcohol (100%) for recrystallization. After cooling to room temperature, diethyl ether was added to the mixture to precipitate more product. The precipitate was filtered and washed with diethyl ether until the precipitate turned white. The resulting precipitate being the product of the reaction, i.e. MAI, was vacuum dried for 5 hours (pressure below 0.2 mbar), after which the product was weighed. A product (MAI) yield of 88% was obtained, comparing to the theoretical yield as per the stoichiometry of the reaction. The composition of the resulting product was subjected to analysis which confirmed the absence of even trace amounts of phosphorus salts since no phosphorus donors were used at any step of the synthesis.

The resulting product was also tested for the presence of phosphorus, and the results obtained were compared with MAI prepared using a method known in the art as well as commercially available MAI. The results are summarized in Table I.

Example II

Synthesis of Octylammonium Iodide (OAI) Without Catalyst

A portion of iodine ($I_2$) was dissolved in ethanol in a round-bottomed flask in a single step to obtain a non-translucent dark brown solution demonstrating the presence of molecular iodine ($I_2$). After 15 minutes, the iodine dissolved in ethanol with the solution remaining dark brown and non-translucent. Formic acid was then added to the flask, in the molar ratio $HCOOH:I_2$ of 0.97:1.0 with no changes observed in the flask. 2.6 moles of octylamine per each mole of $I_2$ iodine were then slowly added dropwise to the solution. After adding each drop of octylamine, gas bubbles and foam appeared in the reaction solution, and the temperature of the reaction mixture was observed to increase due to its exothermic course. Gas bubbles and foam demonstrated that octylamine reacted with hydrogen iodide HI produced in situ. After adding total octylamine (the reaction mixture remained brown), the flask was heated for 2 hours while maintaining the temperature of the reaction mixture at 80° C. The reaction was then terminated, and the resulting mixture had a lighter brown colour, however, the colour of the mixture was not considered to be an indicator of the termination of the reaction due to the excess iodine ($I_2$) used, which prevented it from being completely reacted. The use of excess iodine with respect to formic acid prevented the formation of octylamine formate, which would be a by-product of the synthesis, and thus a contamination of the resulting octylammonium iodide (OAI). When the reaction was over, the mixture was evaporated on a rotary evaporator under reduced pressure of 30 mbar, keeping the flask with the solution, during the evaporation, in water bath of temperature 50° C., to obtain as a result of the evaporation a yellow and brown powder which was then dissolved in boiling absolute ethanol for recrystallization in 1 mL of absolute ethanol per 1 g of the expected product (the assumed yield was 1 mL/1 g). The solution was then cooled and diethyl ether was added to the cooled mixture to increase the precipitation efficiency. This was filtered to obtain a white precipitate, which was washed with diethyl ether until the precipitate turned white. The resulting precipitate constituting the reaction product (OAI) was vacuum dried (pressure below 0.2 mbar) for 5 hours, after which the product was weighed. A product (OAI) yield of 76% was obtained, comparing to the theoretical yield as per the stoichiometry of the reaction.

Example III

Synthesis of Formamidinium Iodide (FAI) Without Catalyst

A portion of iodine ($I_2$) was dissolved in ethanol in a round-bottomed flask in a single step to obtain a non-translucent dark brown solution demonstrating the presence of molecular iodine ($I_2$). After 15 minutes, the iodine dissolved in ethanol with the solution remaining dark brown and non-translucent. 1.0 Eq (equivalent) of formic acid HCOOH (with respect to iodine ($I_2$)) was then added to the flask with no changes observed in the flask. Formamidine acetate (solid at room temperature) was then added to the solution in a single step in a total amount of 2.1 Eq (equivalents) of formamidine acetate (with respect to iodine ($I_2$)). After adding formamidine acetate (the reaction mixture remained brown), the flask was heated for 12 hours, maintaining the reaction mixture temperature at 50° C. The reaction was then terminated, and the resulting mixture had a lighter brown colour. When the reaction was over, the mixture was evaporated on a rotary evaporator under reduced pressure of 30 mbar, keeping the flask with the solution being evaporated in a 50° C. water bath to obtain as a result of the evaporation a yellow and brown powder which was then dissolved in boiling absolute ethanol for recrystallization in 1 mL of absolute ethanol per 1 g of the expected product (the assumed yield was 1 mL/1 g). The solution was then cooled to room temperature and diethyl ether was added to the cooled mixture to increase the precipitation efficiency. This was filtered to obtain a white precipitate, which was washed with diethyl ether until the precipitate turned white. The resulting precipitate constituting the reaction product (FAI) was vacuum dried (pressure below 0.2 mbar) for 5 hours, after which the product was weighed. A product (FAI) yield of 82% was obtained, comparing to the theoretical yield as per the stoichiometry of the reaction.

The resulting product was also tested for the presence of phosphorus. The results are summarized in Table I below.

TABLE I

| | Phosphorus (P) content [%] | MAI/FAI purity (with respect to iodine content [%]) |
|---|---|---|
| MAI (obtained using a known method, without recrystallization) | 0.281 | 97.26 |
| MAI (obtained using a known method, double recrystallization) | 0.041 | 98.05 |
| MAI (according to the disclosure) | 0% (not detected) | 99.47 |
| MAI (commercially available, manufacturer I) | 0.486 | 93.61 |
| MAI (commercially available, manufacturer II) | 0.688 | 92.37 |
| FAI (according to the disclosure) | 0% (not detected) | 99.50 |

Example IV

Preparation of a Perovskite-Forming Composition in a Form of Ink, Using MAI as the Perovskite Precursor The perovskite-forming composition was prepared by dissolving the following compounds in 954 μL of dimethylformamide (DMF):
  305.14 mg of methylammonium iodide (MAI) prepared according to the procedure of Example I above,
  166.50 mg of anhydrous lead (II) acetate $Pb(CH_3COO)_2$,
  35.58 mg lead (II) chloride $PbCl_2$
  solution of dihydrogen phosphate (I) methylammonium $CH_3NH_3H_2PO_2$ in DMF at a concentration of 19.8 mg/mL in the amount of 46 μL (corresponding to 0.3% $CH_3NH_3H_2PO_2$ by weight with respect to the weight of MAI used).

The ingredients were mixed for 12 hours, after which the resulting colloidal solution was filtered using a 0.45 μM filter to obtain a colloid with a suitable particle size of the dispersed phase.

The resulting composition had the form of a stable colloid, suitable for printing (ink). No changes in colloidal particle sizes and no agglomeration tendency have been observed. During several weeks of observation the composition remained in form of a clear (translucent) colloidal solution.

The obtained colloid (containing single-crystallized MAI) is shown in the images: I, II, III, IV, FIG. 14A—the images show the same sample of the colloid, wherein image I shows a sample of the colloid on the day of its preparation, image II shows the colloid 24 hours after its preparation, image III shows the colloid 96 hours after its preparation, and image IV shows said colloid 168 hours after its preparation, which confirms that the clarity of the colloid has not changed over time. For comparison, FIGS. 14B, 14C and 14D show images of the colloid with the identical composition, with FIG. 14B showing images of a colloid containing conventionally prepared, commercially available MAI (using no HI produced in situ); FIG. 14C shows a colloid with MAI prepared using a method known in the art—a colloid containing single-recrystallized MAI, while FIG. 14D shows a colloid with MAI obtained by a method known in the art—a colloid containing triple-recrystallized MAI. FIG. 14B shows, like FIG. 14A, the following photographs: I, II, III and IV of the same colloid sample, taken respectively: I—on the day of its preparation, II—24 hours, III—96 hours and IV—168 hours after its preparation, FIG. 14C, I shows a image of the colloid taken on the day of its preparation, and FIG. 14C, II—72 hours after the preparation of said colloid, and, likewise: FIG. 14D, I—image of the colloid on the day of its preparation, and FIG. 14D, II—an image taken 72 hours after the preparation of said colloid, and FIG. 14D, III—an image taken 144 hours after the preparation of the colloid, which illustrates the change over time in the clarity of the MAI-containing colloid prepared using a method known in the art, which is due to the presence of phosphorus salts in the colloid of FIGS. 14B and 14C. It should be noted that only for the colloid prepared from triple-recrystallized MAI, after 144 hours there is no visible turbidity (for the naked eye), which is also observed for the colloid prepared using MAI of the invention, but subjected to single recrystallization. This further demonstrates superior parameters of iodide (MAI) prepared using the inventive method.

All photographs of FIGS. 14A, 14B, 14C and 14D were taken illuminating the colloids with a flashlight in order to show the Tyndall effect, under the same lighting conditions. Therefore, the study conducted confirmed the improved stability over time of the MAI-containing colloid prepared using the inventive method (FIG. 14A) as well as the overall improved clarity of said colloid.

Thus, the perovskite-forming composition prepared in the form of a colloidal solution contains the inventive MAI as one of the perovskite-forming ingredients.

Example V

Preparation of Perovskite Coatings Using MAI

Three perovskite-forming compositions were prepared as follows:
  composition I, containing ingredients the same as the perovskite-forming composition of example IV above, using MAI obtained by a method known in the art
  composition II, containing ingredients the same as the perovskite-forming composition of example IV above, but without the addition of $CH_3NH_3H_2PO_2$,
  composition III, containing ingredients the same as the perovskite-forming composition of example IV above, wherein used MAI is the MAI obtained by the method according to the present disclosure and with the addition of $CH_3NH_3H_2PO_2$).

Next, a substrate was prepared for the application of the composition of: I, II and III accordingly, as follows: plates were cut out of the PET/ITO (ethylene terephthalate/indium tin oxide) board by means of a laboratory punch and then, by immersion, etched in a 15% hydrochloric acid (HCl) solution to obtain the desired pattern in the ITO conductive layer. The etched plates were cleaned in an ultrasonic bath (cleaning solutions used: deionized water, isopropyl alcohol). The substrates thus prepared were air-dried for 1 hour at 95° C., and then PEDOT:PSS (poly(3,4-ethylene-1,4-dioxyethiophene:styrene polysulphonate) was applied on cleaned and dried substrates using the method of spin-coating in air. Substrates were then heated for 45 minutes at 95° C. in air. Respective perovskite-forming compositions: composition I, composition II, composition III were then applied on the respective plates using the spin-coating technique under nitrogen atmosphere (inside the glove chamber). In order to crystallize the perovskite material, the substrate coated with films of respective perovskite-forming compositions: composition I, composition II, composition III, were heated at 96° C. for 15 minutes.

Figure 7A:
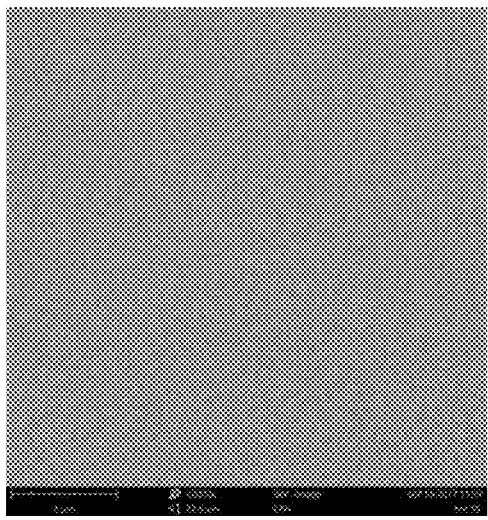
Figure 7B:
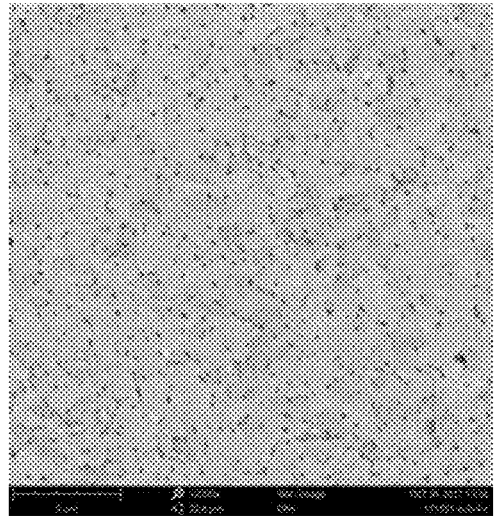
Figure 7C:
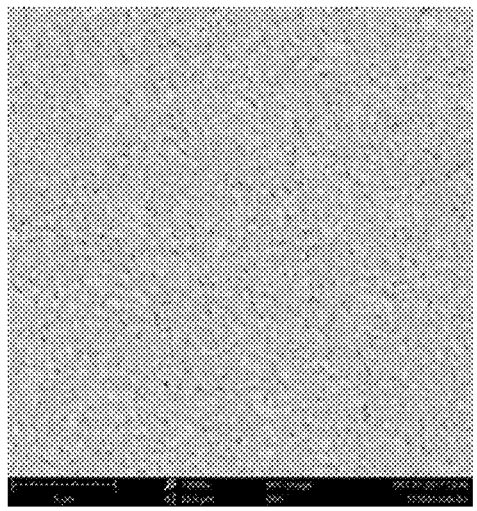

The resulting perovskite coatings, in the form of thin films, on PEDOT/PET/ITO substrates, were then viewed under scanning electron microscope (SEM), and images were taken that are presented in FIG. 7, wherein FIG. 7A is a SEM image of a perovskite coating prepared with composition I, containing in its composition MAI prepared using a method known in the art, FIG. 7B is a SEM image of a perovskite coating prepared with composition II, containing in its composition MAI prepared using the method according to the present disclosure, but without added $CH_3NH_3H_2PO_2$, while FIG. 7C is a SEM photograph of a perovskite coating prepared with composition III, containing in its composition MAI prepared using the method according to the present disclosure, and with added $CH_3NH_3H_2PO_2$.

The results of the SEM analysis of perovskite coatings prepared with compositions I, II and III confirmed the improved morphology of perovskite coatings prepared with MAI obtained using the method according to the present disclosure.

As shown in the photograph in FIG. 7A, the perovskite layer (with prior art MAI) is compact, i.e. it does not contain any pinholes and it features small grains of perovskite material The perovskite layer of FIG. 7B prepared using MAI obtained using the method according to the present disclosure features larger grains and improved crystallinity, which is more advantageous for the operation of the cell; also, pinholes are visible in the layer.

Now, the layer of FIG. 7C prepared using the MAI, obtained by the method according to the present disclosure with added $CH_3NH_3H_2PO_2$, also features larger grains and, additionally, reduced quantity of pinholes. This may be achieved by the addition of $CH_3NH_3H_2PO_2$ in the amount of 0.3% $CH_3NH_3H_2PO_2$ by weight with respect to the weight of MAI, which allows for adjusting the chemical parameters of the perovskite-forming composition being a colloidal solution to obtain an optimised morphology of the perovskite layer.

The resulting coatings were also analysed using X-ray diffraction tests, with the diffractograms obtained presented in FIG. 8, wherein FIG. 8A shows diffractions of $CH_3NH_3PbI_3$ perovskite network, FIG. 8B shows an enlarged peak corresponding to the reflection (110) in the tetragonal plane of the perovskite phase, while FIG. 8C shows an enlarged (control) peak corresponding to the PET material—differences between samples are negligible.

The thickness measured using an optical profilometer was the same for all the coatings obtained with the compositions: I, II and III, so the differences in intensity of peaks in diffractograms were not due to the amounts of perovskite material varying between samples. The obtained X-ray diffractograms demonstrated, for the samples with the MAI prepared according to the present disclosure (composition II and III), a higher intensity of peaks corresponding to perovskite reflections positions, especially the peak at 14° corresponding to the reflection (110) in the tetragonal symmetry of the perovskite material (FIG. 8B). This may be due to the formation of a higher share of crystalline phase and/or a higher level of orientation of perovskite grains, which is particularly advantageous for photosensitive perovskite coatings for optoelectronic applications, and may provide improved functionality when said coatings are used in solar cells.

Example VI

Preparation of Perovskite Photovoltaic Cells Using MAI

In order to produce photovoltaic cells with a photoactive perovskite layer, perovskite compositions were prepared with the composition as in example V above, namely:
composition I, containing ingredients as the perovskite-forming composition of example IV above, using MAI obtained using a method known in the art,
composition II, containing ingredients as the perovskite-forming composition of example IV above, containing the MAI according to the present disclosure (with HI produced in situ) but with no $CH_3NH_3H_2PO2$ added,
composition III, containing ingredients as the perovskite-forming composition of example IV above, wherein used MAI is the MAI obtained by the method according to the present disclosure, and with the addition of $CH_3NH_3H_2PO_2$).

The above compositions were used to prepare photovoltaic cells with a simple sandwich architecture containing the following layers: PET/ITO/PEDOT:PSS/ perovskite: $CH_3NH_3PbI_3$/PCBM/BCP/Ag.

For this purpose, substrates containing respective layers of PET/ITO/ PEDOT:PSS/perovskite: $CH_3NH_3PbI_3$ were prepared for each cell separately from the above perovskite-forming compositions: I, II and III.

PCBM (phenyl-C61-butyric acid methyl ester) solution dissolved in anhydrous chlorobenzene at a concentration 20 mg/mL was deposited on the perovskite layer of each cell using the spin-coating method under nitrogen (inside glove chamber) immediately after the perovskite layer was obtained. For each cell, the PCBM layer after deposition was heated for 10 minutes at 60° C.

5 nm BPC (bathocuproine) and 90 nm silver (Ag) layers were then sequentially thermally vapour-deposited one by one at a predetermined pressure of $1·10^{-6}$ mbar. The characteristics of the obtained cells are presented in FIG. 9A, presenting the results of measurement of cell efficiency ($\eta$) determining the energy conversion efficiency of a cell, depending on the type of perovskite-forming composition: I, II and III for the perovskite layer of the cell. The results of the measurements confirmed the improved efficiency of the cells with the perovskite layer of the perovskite composition II with the inventive MAI and showed a further substantial improvement in the efficiency of the cells with the perovskite layer of composition III with the inventive MAI and added $CH_3NH_3H_2PO_2$ compared to the cell containing the perovskite layer of composition I with prior art MAI.

FIG. 9B, on the other hand, is a summary of the results of tests presenting dependence: current density-voltage, which also confirmed improved parameters of the cells with the perovskite layer made of the composition: II and III containing the MAI obtained according to the method of the present disclosure. As shown in the graph of FIG. 9B, the average efficiency of cells with the perovskite layer is composition II is 8.2%, while the efficiency of cells with the perovskite layer of prior art composition I ranges from 7.2 to 8.0%, which indicates an improvement in cell efficiency at the level of 2.5 to 14%. Cells with the perovskite layer made of composition III (containing the MAI according to the disclosure and $CH_3NH_3H_2PO_2$) showed an additional increase in efficiency, both for the cells of composition I and those of composition II. The efficiency of cells of composition III ranged from 9.0 to 9.2%.

In addition, during the course of the work it was found that the cells with the perovskite layer made of compositions II and III exhibit improved reproducibility and long-term stability of operation compared to the cells with the perovskite layer made of composition I containing prior art MAI, which is due to the difference in the density of defects of the perovskite layer made of the respective composition: I, II, III.

Furthermore, ageing tests were carried out for selected cells: ageing at the maximum power point with continuous sunlight of 800 W/m$^2$ in an inert atmosphere and at a temperature of 32° C. The results of these tests, summarized in FIG. 10 have shown that cells containing the perovskite layer with the inventive MAI show good performance for an extended period of time. In particular, the use of the MAI obtained according to the present disclosure enables greater control over the quality of the layer of the perovskite obtained, including, in particular, greater crystallinity of the perovskite layer, which may result in improved stability of the cell produced with such perovskite.

Example VII

Preparation of a Perovskite-Forming Composition Using FAI

The perovskite-forming composition was prepared by dissolving the following compounds in the mixture of 400 μL dimethylformamide (DMF) and 100 μL of dimethyl sulphoxide (DMSO):
  95.01 mg of formamidinium iodide (FAI) prepared according to the procedure of Example III above,
  38.53 mg of methylammonium bromide $CH_3NH_3Br$,
  274 mg of lead (II) iodide $PbI_2$
  a solution of caesium iodide (CsI) in toluene at concentration of 2M.

The ingredients were mixed for 12 hours, after which the resulting colloidal solution was filtered using a 0.45 μM filter to obtain a colloid with a suitable particle size of the dispersed phase.

The resulting composition had the form of a stable colloid. No changes in colloidal particle sizes and no agglomeration tendency have been observed (which is the case for colloids containing prior art FAI). During several weeks of observation, the composition had the form of a clear (translucent) colloidal solution.

Thus, the perovskite-forming composition prepared in the form of a colloidal solution contains the inventive FAI as one of the perovskite-forming ingredients (perovskite precursors).

Example VIII

Preparation of Perovskite Coatings Using FAI

Two perovskite-forming compositions were prepared as follows:
  composition I, containing ingredients the same as the perovskite-forming composition of Example VII above, but using FAI obtained by a method known in the art,
  composition II containing ingredients the same as the perovskite-forming composition of Example VII above, but containing the FAI prepared by the method according to the present disclosure.

The substrate was then prepared for depositing compositions I and II as described in Example V above. A layer of PTAA (poly[bis(4-phenyl)(2,4,6-trimethylphenyl)amine]) in toluene was then applied onto the plates by spin-coating a PTAA solution in toluene (concentration of 2 mg/mL, solution filtered using a 0.2 μm filter). Composition I (control) and composition II, respectively, were then applied on the substrates using the spin-coating technique, under nitrogen, with the following predetermined parameters: spinning time: 30 seconds, acceleration: 2500 rpm, rotational speed: 2500 rpm. During the last, 8$^{th}$ second of coating, ethyl acetate (as an anti-solvent) in the amount of 1000 μL pereach plate was added dropwise onto the films being prepared. The films were then heated at 100° C. for 40 minutes to obtain perovskite structures.

The resulting perovskite coatings, in a form of thin films, on substrates, were then viewed under scanning electron microscope (SEM), and images were taken that are presented in FIG. 11, wherein FIG. 11A is a SEM image of a perovskite coating prepared with composition I, containing in its composition FAI prepared using a method known in the art, while FIG. 11B is a SEM image of a perovskite coating prepared with composition II, containing in its composition FAI prepared using the method according to the present disclosure.

The results of the SEM analysis conducted of perovskite coatings prepared with compositions I, II confirmed good morphology of perovskite coatings prepared with FAI obtained using the developed method. The images show larger grains of perovskite material obtained from the inventive FAI compared to the perovskites prepared with prior art FAI.

The resulting coatings were also analysed using X-ray diffraction tests, with the diffractograms obtained presented in FIG. 12, wherein FIG. 12A shows the diffraction of the network of the perovskite obtained: $Cs_{0.1}(FA_{0.83}MA_{0.17})_{0.9}Pb(I_{0.84}Br_{0.16})_3$, where MA is the methylammonium moiety, and FA is the formamidinium moiety; FIG. 12B shows an enlarged peak corresponding to the reflection (100) for the cubic perovskite phase.

The thickness measured using an optical profilometer, was the same for all the coatings obtained with the compositions: I and II, so the differences in intensity of peaks in diffractograms were not caused by different amounts of perovskite material varying between samples. The obtained X-ray diffractograms demonstrated, for the samples with the FAI according to the present disclosure (composition II) a higher intensity of peaks corresponding to perovskite reflections positions, especially (100) in the cubic perovskite phase (FIG. 9B). This may be due to the formation of a higher share of crystalline phase and/or a higher level of orientation of perovskite grains, which is particularly advantageous for photosensitive perovskite coatings for optoelectronic applications.

Example IX

Preparation of Perovskite Photovoltaic Cells Using FAI

In order to produce photovoltaic cells with a photoactive layer of perovskite, perovskite compositions were prepared with the ingredients as in example VIII above, containing the FAI according to the present disclosure (composition II—with HI prepared in situ).

The composition as above was used to prepare a photovoltaic cell with a simple sandwich architecture containing the following layers: PET/ITO/PTAA/perovskite: $Cs_{0.1}(FA_{0.83}MA_{0.17})_{0.9}Pb(I_{0.84}Br_{0.16})_3$/PCBM/BCP/Ag.

For this purpose, a substrate containing respective layers of PET/ITO/PTAA/ perovskite were prepared: $Cs_{0.1}(FA_{0.83}MA_{0.17})_{0.9}Pb(I_{0.84}Br_{0.16})_3$.

The respective PCBM, BCP and Ag layers were then applied using the same method as described in Example VI above.

The invention claimed is:

1. A method for obtaining a salt having a general formula: $R_xNI$, wherein:
   $R_xN$ is an organic cation ($R_xN^+$),
   wherein R represents substituents (R—) independently selected from a group consisting of organic substituents: $R^1$—, $R^2$—, $R^3$— and hydrogen (H—), wherein the donor of organic cation $R_xN^+$ contains as organic substituents: $R^1$—, $R^2$— and optionally $R^3$— moieties independently selected from a group consisting of: straight chain or branched chain alkyl substituents containing 1 to 8 carbon atoms in a substituent molecule,
   x is a number of the substituents R— directly linked with the nitrogen (N) atom in the organic cation $R_xN^+$, wherein x is 3 or 4,
   I is an iodide anion ($I^-$),
   the method comprising the steps of:
   preparing a reaction mixture by:
     synthesizing hydrogen iodide (HI) in situ by mixing molecular iodine ($I_2$) with formic acid (COOH) in a molar ratio of molecular iodine ($I_2$): formic acid (COOH) of no less than 1.01:1, in a solvent medium,
     introducing into the solvent medium a compound being a donor of an organic cation $R_xN^+$ in an amount providing the molar ratio of the donor of the organic cation $R_xN^+$: molecular iodine ($I_2$) of no less than 1.01:1, and
     maintaining the reaction mixture at a temperature of not less than 20° C. for a time necessary to obtain a reaction product being the salt having the general formula $R_xNI$.

2. The method according to claim 1, wherein molecular iodine ($I_2$) is mixed with formic acid (HCOOH) at a molar ratio: molecular iodine ($I_2$): formic acid (COOH) of 1.01:1 to 1.1:1, and the donor of the organic cation $R_xN^+$ is introduced to the solvent medium in an amount providing a molar ratio of the donor of organic cation $R_xN^+$: molecular iodine ($I_2$) of 1.01:1 to 1.50:1.

3. The method according to claim 1, wherein molecular iodine ($I_2$) is mixed with formic acid (HCOOH) at a molar ratio of iodine ($I_2$): formic acid (COOH) of 1.01:1.

4. The method according to claim 1, wherein the reaction mixture is heated to a temperature in a range from 20 to 80° C.

5. The method according to claim 1, wherein the donor of the organic cation $R_xN^+$ is introduced to the solvent medium following the synthesis in situ of hydrogen iodide (HI).

6. The method according to claim 1, wherein amine is used as a donor of the organic cation $R_xN^+$, and the obtained salt ($R_xNI$) contains the organic cation ($R_xN^+$) selected from the group consisting of: alkylammonium cations ($R(H_3)N^+$), dialkylammonium cations $R_2(H_2)N^+$, and trialkylammonium cations ($R_3(H)N^+$).

7. The method according to claim 6, wherein primary alkylamine with the general formula $RNH_2$ is used as the donor of organic cation $R_xN^+$, and the obtained salt: alkyl ammonium iodide has the general formula of $R(H_3)NI$, where the substituent R represents an alkyl moiety containing 1 to 8 carbon atoms.

8. The method according to claim 6, wherein methylamine is used as the donor of organic cation $R_xN^+$, and methylammonium iodide (MAI) is obtained as the salt.

9. The method according to claim 6, wherein octylamine is used as the donor of organic cation $R_xN^+$, and octylammonium iodide (OAI) is obtained as the salt.

10. The method according to claim 1, wherein an amidine salt is used as the donor of organic cation $R_xN^+$ and amidinium iodide ($R_2N$—($R^3$)C=$N(H_2)I$) is obtained as the salt.

11. The method according to claim 10, wherein formamidine acetate is used as the donor of organic cation $R_xN^+$ and formamidinium iodide (FAI) ($H_2N$—C(H)=$N(H_2)I$) is obtained as the salt.

12. The method according to claim 1, wherein the solvent medium comprises at least one compound selected from a group consisting of: methanol, ethanol, absolute ethanol, isopropanol, dioxane, tetrahydrofuran (THF) and dimethylformamide (DMF).

13. The method according to claim 8, wherein the solvent medium is water.

14. The method according to claim 1, wherein preparing a reaction mixture further comprises the step of introducing, into the solvent medium, a catalyst being a salt with the general formula $R_xNI$.

15. The method according to claim 14, wherein the catalyst is a compound identical to the salt $R_xNI$ being the reaction product.

16. The method according to claim 14, wherein the catalyst is introduced at a molar ratio of catalyst: molecular iodine ($I_2$) ranging from 0.01:1 to 0.03:1.

17. The method according to claim 1, wherein wherein R represents substituents (R—) independently selected from a group consisting of organic substituents: $R^1$—, $R^2$—, $R^3$— and hydrogen (H—), wherein the donor of organic cation $R_xN^+$ contains as organic substituents: $R^1$—, $R^2$— and optionally $R^3$— moieties independently selected from a group consisting of: straight chain or branched chain alkyl substituents containing 1 to 8 carbon atoms in a substituent molecule, and at least one heteroatom substituting the carbon atom or hydrogen atom in the substituent molecule, wherein the heteroatom is selected from the group consisting of: silicon, oxygen, nitrogen, sulphur, iodine, chlorine and bromine.

* * * * *